United States Patent [19]

Vallarino et al.

[11] Patent Number: 5,373,093
[45] Date of Patent: Dec. 13, 1994

[54] MACROCYCLIC COMPLEXES OF YTTRIUM, THE LANTHANIDES AND THE ACTINIDES HAVING PERIPHERAL COUPLING FUNCTIONALITIES

[76] Inventors: Lidia M. Vallarino, 1009 West Ave., Richmond, Va. 23220; Robert C. Leif, 5648 Toyon Rd., San Diego, Calif. 92115

[21] Appl. No.: 669,833

[22] Filed: Mar. 15, 1991

Related U.S. Application Data

[63] Continuation of Ser. No. 353,823, May 22, 1989, abandoned, which is a continuation-in-part of Ser. No. 200,220, May 31, 1988, abandoned.

[51] Int. Cl.$^5$ .................. A61K 49/00; A61K 39/395; C07F 5/00; C07D 221/00
[52] U.S. Cl. ........................................ 534/15; 534/10; 530/391.5; 530/402; 530/409; 540/465; 540/474
[58] Field of Search ............... 540/465, 474, 477; 534/10, 15, 16; 530/391.5, 402, 409

[56] References Cited

U.S. PATENT DOCUMENTS

| | | | |
|---|---|---|---|
| 4,454,106 | 6/1984 | Gansow et al. | 424/1.1 |
| 4,678,667 | 7/1987 | Meares et al. | 424/9 X |
| 5,087,696 | 2/1992 | Parker et al. | 424/1.1 X |

OTHER PUBLICATIONS

Derwent Abstract 89-062473/09, Hoescht AG, EP 304,780 A, Aug. 1987.

Desreux et al., *Nucl. Med. Biol.*, vol. 15, No. 1 (1988) pp. 9-15.
Abid et al., *Inorganica Chim. Acta*, vol. 95 (1984) pp. 119-125.

*Primary Examiner*—Robert L. Stoll
*Assistant Examiner*—John M. Covert
*Attorney, Agent, or Firm*—Gerald R. Hibnick

[57] ABSTRACT

Functionalized water soluble macrocyclic complexes of lanthanide, actinide and yttrium ions were obtained by metal templated, Schiff-base, cyclic condensation of: (1) a functionalized 1,2-diaminoethane and a dicarbonyl compound selected from the group consisting of 2,6-dicarbonylpyridine, 2,6-diformylpyridine, 2,5-dicarbonylfuran, 2,5-diformylfuran, 2,5-dicarbonylthiophene and 2,5-diformylthiophene; or (2) 1,2-diaminoethane and a ring-substituted heterocyclic dicarbonyl compound selected from a group consisting of substituted 2,6-dicarbonylpyridine, substituted 2,6-diformylpyridine, substituted 2,5-dicarbonylfuran, substituted 2,5-diformylfuran; substituted 2,5-dicarbonyl thiophene, and substituted 2,5-diformylthiophene. Coordination complexes thus formed are kinetically stable in dilute aqueous solution. They are further reacted, or coupled, through a substituent on the 1,2-diaminoethane or on the pyridine, furan, or thiophene moieties, to one of the following: proteinaceous materials, polysaccharides, other biologically compatible macromolecules or bridging molecules which, can be further reacted or coupled to the above mentioned substrates. These macrocyclic complexes are suitable in the preparation of reporter molecules and for magnetic resonance, radiation imaging and radiation therapy.

37 Claims, No Drawings

MACROCYCLIC COMPLEXES OF YTTRIUM, THE LANTHANIDES AND THE ACTINIDES HAVING PERIPHERAL COUPLING FUNCTIONALITIES

This application is a continuation of application Ser. No. 07/353,823, filed May 22, 1989 now abandoned, which is a continuation-in-part of Ser. No. 07/200,220 filed May 31, 1988 now abandoned.

BACKGROUND OF THE INVENTION

1. Field of the Invention

This invention concerns a process for the synthesis of functionalized, water-soluble, macrocyclic complexes of the lanthanides having atomic numbers 57–71, of the actinides having atomic numbers 89–103, and of yttrium(III) having atomic number 39.

This invention also includes processes for the coupling of such complexes to biologically active or biologically compatible molecules, or to biological cells through peripheral pendant substituents having one or more reactive sites. These complexes are useful particularly as reporter molecules in immunoassays, analytical cytology, histological staining, and imaging processes (Leif et al., Clinical Chemistry, 1977, 23, 1492, Development of Instrumentation and Fluorochromes for Automated Multiparameter Analysis of Cells; Leif et al., 1976, Markers for Instrumental Evaluation of Cells of the Female Reproductive Tract: Existing and New Markers, in The Automation of Uterine Cancer cytology, Ed. Wied, Bahr and Barrels pages 313–345).

2. Description of the Prior Art

The complexation of lanthanide ions with organic as well as inorganic compounds and the subsequent use of the resultant complexes in both industrial and biological environments has been previously reported. Such complexes, also referred to as "coordination compounds", are typically formed by the union of a lanthanide ion with appropriate ligands, which can be negatively charged or ionically neutral.

The complexes of the lanthanide(III) ions with unidentate ligands or bidentate chelating ligands are known to be extremely labile, achieving complexation and ligand-exchange equilibrium almost instantaneously. Thus, even very stable complexes of the lanthanide(III) ions and bidentate chelating ligands, e.g. tris(acetylacetonato)-lanthanum(III) exist in solution as a mixture of species, the uncomplexed (solvated) metal ion being present in an appreciable amount. Lanthanide complexes of fused polychelating non-cyclic ligands are somewhat less labile; whereas, those of cyclic ligands are relatively inert.

The stability and lability of the lanthanide(III)-ligand complex can be critical, depending upon the particular use and/or environment. More specifically, the time frame of metal-exchange and ligand-exchange kinetics is a major consideration when such complexes are used as probes in biological systems. In the dilute aqueous solutions or aqueous-organic solutions required for these systems, often involving contact with potentially competing ligands, such complexes, if labile, can dissociate. Where such dissociation does occur, the value of the probe is diminished or lost. Alternatively, vibrational quenching of the fluorescence by interaction with water molecules may occur. For instance as reported by Evangelista, R. A., A New Europium Chelate for Protein Labelling and Time-Resolved Fluorometric Applications, Clinical Biochemistry, 1988, 21, 173–178, the dinegative anionic ligand 4,7-bis (chlorosulfophenyl)-1,10-phenanthroline-2,9-dicarboxilic acid (BCPDA) forms a fluorescent complex with europium(III). However, this complex is not detected at concentrations required to detect many analytes of interest which are present in picogram or lower concentrations. Since BCPDA complex of europium(III) ion binds sufficient water to quench the fluorescence, the added inconvenient step of drying the samples must be performed prior to measurement. Furthermore, the quantum efficiency of the BCPDA europium(III) complex is relatively low, so that as reported by Khosravi, M. J. and Diamandis, E. P., Time-Resolved Immunofluorometry of Follitropin in Serum, Clinical Chemistry, 35, No. 1, 181 (1989), it was necessary to increase the sensitivity for analytes which are present in low concentration, by binding the chelate to thyroglobulin as an intermediate step to build a multilayer system.

Soini and Lovgren, Time-Resolved Fluorescence of Lanthanide Probes and Applications in Biotechnology, CRC Critical Reviews in Analytical Chemistry Vol. 18., Issue 2 (1987) pages 105–154; Soini and Hemmila, Fluorescence Spectroscopy Assay Means, U.S. Pat. No. 4,374,120, (1983) have reported on the use of a fluorescent chelate of a lanthanide. The ligand was DTPA (WO Patent 03698, 1984), which forms a strong but nonfluorescent complex with europium(III). This complex was dissociated with acid Hemmila et al. Europium as a label in Time-Resolved Immunofluorometric Assays, Anal. Biochem. 137, 335–343 (1984); and the solubilized europium(III) was complexed with a beta-diketone in a micellar phase. These dissociation-complexation steps resulted in an increase in complexity of the procedure; in a decrease in the concentration of the chelate, which limited the sensitivity of the fluorescence measurement; and in a loss of spatial information due to the separation of the fluorophore from the binding moieties. Because of the separation of the fluorescent tag from the specific binding molecule, this technique is incompatible with immunofluorescence or similar measurements on single cells, or other particles by either flow cytometry or microscopy.

The preparation of inert, kinetically stable, non-functionalized macrocyclic complexes of a limited number of lanthanide(III) ions was first reported in the technical literature by Backer-Dirks et al., J.C.S. Chem. Comm. (1979) 774. The synthesis described in this paper involved a metal templated Schiff-base condensation of 2,6-diacetylpyridine with ethylenediamine in the presence of the nitrate salts of lanthanum(III) and cerium-(III). The conditions selected for the condensation were, however, reportedly unsuccessful for the preparation of analogous complexes from the heavier members of the lanthanide series. Because of the high kinetic stability of these complexes and their resistance to dissociation in dilute aqueous solutions, the authors suggested their potential use as aqueous NMR shift reagents.

The synthesis of kinetically stable macrocyclic complexes of the lanthanide(III) ions by metal templated condensation techniques has recently been extended to include all elements within the lanthanide series, except radioactive promethium, $_{61}$Pm.

The following additional references describe known non-functionalized macrocyclic complexes. List A includes publications by at least one of the inventors. List B includes additional publications by others.

LIST A

L. De Cola, D. L. Smailes, L. M. Vallarino, *X Convegno Nazionale Di Fotochimica*, 1985, p.4, Effect of Heteroligands on the Luminescence Properties of Cationic Macrocyclic Complexes of Eu(III) and Tb(III).

L. De Cola, D. L. Smailes, L. M. Vallarino, *Inorganica Chimica Acta*, 110, 1985, L1-L2, Metal-templated Synthesis of Novel Macrocyclic Complexes of the Uranyl Ion.

L. De Cola, D. L. Smailes, L. M. Vallarino, *Inorganic Chemistry*, 1986, 25, 1729, Hexaaza Macrocyclic Complexes of the Lanthanides.

G. Bombieri, F. Benetollo, A. Polo, L. De Cola, D. L. Smailes, L. M. Vallarino, *Inorganic Chemistry*, 1986, 25, 1127, Synthesis, Characterization, and Crystal Structure of a Hexaaza Macrocyclic Complex of Lutetium(III).

N. Sabbatini, L. De Cola, L. M. Vallarino, G. Blasse, *J. Phys. Chem*, 1987, 91, 4681-4685, Radiative and Nonradiative Transitions in the Eu(III) Hexaaza Macrocyclic Complex $[Eu(C_{22}H_{26}N_6)(CH_3COO)](CH_3COO)Cl\cdot 2H_2O$.

G. Bombieri, L. De Cola, A. Polo, D. L. Smailes, L. M. Vallarino, *Virginia Journal of Science*, 1987, 38, 95, Condensation of 2,6-Diacetylpyridine and 1,2-Diaminobenzene in the Presence of Lanthanide Ions.

F. Benetollo, G. Bombieri, W. T. Hawkins, A. Polo, L. M. Vallarino, *Division of Inoganic Chemistry*, 1987, 193, Synthesis, Structure, and Properties of Y(III) Macrocyclic Complexes.

A. Polo, J. R. Quagliano, L. M. Vallarino, *Virginia Journal of Science*, 1988, 39, 140, Lanthanide Complexes of a Six-Nitrogen Analog of 18-Crown-6.

W. T. Hawkins II, A. Polo, L. M. Vallarino, *Journal of American Chemical Society*, 1987, 19, 36, Synthesis of Six-Nitrogen-Donor Macrocyclic Complexes of Yttrium(III).

LIST B

A. M. Arif, J. D. J. Backer-Dirks, C. J. Gray, F. A. Hart, M. B. Hursthouse, *J. Chem. Soc.*, 1987, 1665, Syntheses, X-Ray Structures, and Properties of Complexes of Macrocyclic Hexamines with Lanthanide Nitrates.

K. K. Abid, D. E. Fenton, *Inorganica Chimica Acta*, 82(1984) 223-226, The Synthesis of Macrocyclic Lanthanide Complexes Derived from 2,5-Furandialdehyde and alpha, omega-Alkanediamines.

B. Bombieri, *Inorganica Chimica Acta*, 139(1987) 21-32, New Trends in the Structural Chemistry of Actinide and Lanthanide Coordination Compounds.

W. Radecka-Paryzek, *Inorganica Chimica Act*, 109(1985) L21-23, The Template Synthesis and Characterization of Hexaaza 18-Membered Macrocyclic Complexes of Cerium(III), Praseodymium(III) and Neodymium(III) Nitrates.

K. K. Abid, D. E. Fenton, *Inorganic Chimica Acta*, 95(1984) 119-125, Lanthanide Complexes of Some Macrocyclic Schiff Bases Derived from Pyridine-2,6-dicarboxyaldehyde and alpha, omega-Primary Diamines.

W. Radecka-Paryzek, *Inorganica Chimica Acta*, 45(1980) L147-148, Template Synthesis and Characterization of 18-Membered Hexaaza Macrocyclic Complex of Lanthanum(III) Perchlorate.

V. K. Manchanda, C. A. Chang, *Anal. Chem.*, 1987, 813-818, Solvent Extraction Studies of Europium(III), Ytterbium(III), and Lutetium(III) with Ionizable Macrocyclic Ligands and Thenoyltrifluoroacetone.

W. Radecka-Paryzek, *Inorganica Chimica Acta*, 52(1981) 261-268, The Synthesis and Characterization of the Macrocyclic and Ring-opened Complexes Formed in the Reaction of the Lanthanides with 2,-6-diacetylpyridine and Hydrazine.

E. E. Fenton, P. A. Vigato, *Chem, Soc, Rev.*, 1988, 17, 69-90, Macrocyclic Schiff Base Complexes of Lanthanides and Actinides.

In the syntheses described in the Vallarino papers cited in List A, macrocyclic complexes were prepared from all lanthanide(III) ions, except radioactive promethium, by metal templated condensation of 2,6-diacetylpyridine and 1,2-diaminoethane (ethylenediamine). The success of the Vallarino technique in preparing macrocyclic complexes from the heavier lanthanides was believed to be favorably influenced by the specific counterion present in the reaction medium. More specifically, when Vallarino carried out the metal templated condensation in the presence of a lanthanide acetate, instead of the previously used nitrate or perchlorate salts, the formation of the macrocycles was extended to lutetium; furthermore, greatly improved yields and purity of the resultant complex were observed. The use of a lanthanide acetate as the source of lanthanide ions was thus preferred.

The macrocyclic complexes obtained by Vallarino et al. exhibited a kinetic stability and resistance to dissociation in dilute aqueous solutions that made them suitable for the staining of cytological specimens. Adaptation of these lanthanide macrocyclic complexes to the imaging science, as well as to fluorescent immunoassay, requires their derivatization to permit their coupling to a biological substrate or to other reactive groups and/or entities. Such functionalization has not as yet been reported.

There have been other attempts at exploiting the unique properties of lanthanides in both the industrial and the biological environments. In each instance, the lanthanide(III) ion was associated with a chelating ligand. Some processes involved, or were related to, the use of lanthanide-ligand complexes in a "time-gated" fluorescence detection system, reportedly suitable in both solid and fluid phase fluorescence microscopy. Wieder et al. in U.S. Pat. No. 4,352,751 described the chelation of lanthanide ions with a species-linked diaminetetraacetic acid, and the use of such chelates in conjunction with a "sensitizer". The sensitizer was used to increase the fluorescence excitation efficiency of these lanthanide chelates. The lanthanide chelates could be further derivatized by incorporation of so-called "target molecules"; that is, of compounds which immunochemically mimicked the analyte of interest and, thus, could compete with the analyte of interest for an antibody specific to the analyte.

The derivatization of the chelates also contemplated the presence of a "spacer" unit, which reportedly was linked to the chelate and could serve as a point of further derivatization or attachment to the target molecules. The use of "spacer" units was recommended where the chelates were to be used in conjunction with "biologically active target molecules", i.e. therapeutic drugs, enzymes, hormones, peptides and other types of macromolecules which are typically analyzed by immunoassay. Wieder's disclosure was, however, relatively uninformative as to what type of spacer units were to be used, the criteria for their selection, and how and under what conditions the chelate could be appropriately modified to incorporate such spacer units.

Notwithstanding the relative success reported by Wieder for his species-linked diaminetriacetic acid compounds as chelating agents for lanthanide ions, further improvement is still needed in the development of lanthanide-ligand complexes for use in bioanalytical environments, and specifically for immunoassay. In particular, there still exists a need for a lanthanide composition which can be readily adapted (conjugated) to biologically active materials without substantial alteration in its kinetic stability and desired physical properties. The desired properties can include, for example, high fluorescence excitation efficiency and suitable lifetime for complexes intended as fluorescent probes, or high relaxivity toward the protons of water for complexes intended as in vivo magnetic resonance contrast agents.

This invention has addressed the deficiencies in the prior art by providing a series of water-soluble hexa-aza-macrocyclic complexes, also hereinafter referred to as "macrocyclic complexes", incorporating a lanthanide, actinide or yttrium ion, wherein such complexes possess high kinetic stability and pendant functional group(s) that can be readily coupled/conjugated to a biologically active molecule such as an antibody or antigen, or to a biologically compatible ionically uncharged macromolecule, such as a linear or cross-linked polysaccharide. The functional group(s) can be incorporated into the macrocyclic structure either before or after the condensation reaction. Furthermore, the macrocyclic complexes possess the properties desired for their intended use. For example, the complexes of europium(III) and terbium(III) possess a long-lived fluorescence intensity that can be substantially increased by interaction with a suitable enhancer; whereas, the complexes of gadolinium(III) possess high relaxivity.

SUMMARY OF THE INVENTION

The macrocyclic complexes of this invention, having a lanthanide, actinide, or yttrium ion as the metal center and carrying peripheral coupling functionalities, are represented by the following general formulas: I and II. In Formula I the substituent Q is attached directly to the macrocycle ring, and in Formula II the substituent Q is attached to the aromatic moiety.

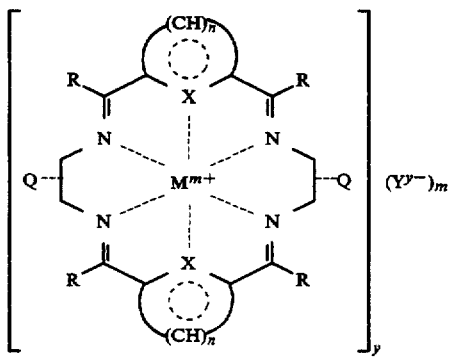

and

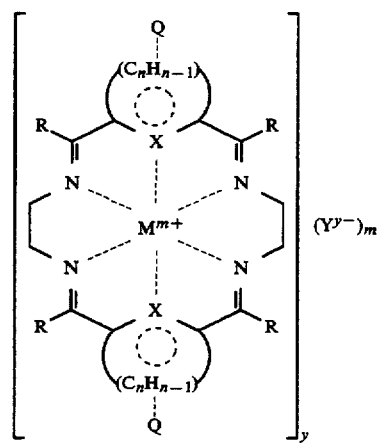

wherein in both formulas I and II R is a substituent selected from the group consisting of hydrogen, methyl, straight-chain alkyl, or branched-chain alkyl; aryl-substituted alkyl, aryl, and alkyl-substituted aryl, with the proviso that such substituent does not limit the solubility of the resultant complex or otherwise interfere with the cyclization of such complex during its synthesis; M is a metal ion selected from the group consisting of a lanthanide having atomic number 57–71, an actinide having atomic number 89–103 and yttrium(III) having atomic number 39;

X is selected from the group consisting of nitrogen, sulfur and oxygen which forms a part of a ring structure selected from the group consisting of pyridine, thiophene or furan, respectively, at the positions marked X;

Q is a substituent selected from the group consisting of functionalized methyl, functionalized straight-chain alkyl, functionalized branched-chain alkyl; functionalized aryl-substituted alkyl, functionalized aryl, and functionalized alkyl-substituted aryl, with the proviso that groups of said substituent provide coupling functionality between said substituent and a bridging/linking moiety to permit the derivatization thereof with a receptor molecule or an entity for which there is a corresponding receptor molecule;

n is an integer selected from the group consisting of 2 and 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex, and;

y is the ionic charge of the counterion in the macrocyclic complex.

The macrocyclic complexes depicted above are prepared by the lanthanide, actinide, or yttrium templated cyclic Schiff-base condensation of a 2,6-dicarbonylpyridine, or its furan or thiophene analog, with a 1,2-diaminoethane, with either the dicarbonyl- or the diamino- precursor carrying the desired pendant coupling functionality. In the alternative, the coupling functionality is added in a subsequent reaction.

The functionalized diamino- precursor is prepared by converting a substituted alpha-amino acid to the corresponding 1,2-diaminoethane derivative. Where the amino acid has other functional groups which are sensitive to reduction or amination, these groups are protected in the conventional manner.

Once the functionalized 1,2-diaminoethane derivative has been prepared, it is combined with a 2,6-dicarbonylpyridine, or its furan or thiophene analog, and with a salt of a lanthanide, actinide or yttrium ion, preferably the acetate salt. The metal ion provides a geometric template for the cyclic 2:2 condensation of the dicarbonyl compound with the 1,2-diamino derivative. The condensation is carried out preferably in an anhydrous alcohol, such as methanol or ethanol. The reaction product, notably the lanthanide, actinide or yttrium macrocyclic complex, is recovered as a solid residue from the reaction medium by vacuum evaporation. The solid residue is then recrystallized to yield a crystalline product, the composition and structure of which correspond to the desired macrocyclic complex, as confirmed by chemical and spectroscopic analysis.

The functionalized dicarbonyl precursor can be prepared from the corresponding functionalized heterocycle by any one of the appropriate methods known in the literature. If necessary, the functional group is protected prior to the transformation into the dicarbonyl derivative. The functionalized dicarbonyl compound is then reacted with 1,2-diaminoethane in the presence of a metal salt as a template, under the above indicated conditions, to produce the metal-macrocycle functionalized at the heterocyclic moiety.

The macrocyclic complexes have various uses depending upon the unique properties of each central metal ion, upon the other constituents of the complex, and upon the interactions between the lanthanide ion and any other constituents of the complex.

The pendant functional groups are further reacted (conjugated) with biologically active molecules, i.e. antibodies, antigens, binding proteins, polysaccharides and/or analytes of interest. This conjugate is then used in analytical procedures, e.g. fluorescent immunoassay; in the identification of biological products, i.e. cells, proteins and low molecular weight substances; in histological staining; in nuclear magnetic resonance or nuclear imaging; and in immunotherapy. More specifically, the conjugates of this invention are used as an injectable solution for administration to a recipient for in vivo observation and/or labelling of a target tissue in accordance with standard diagnostic imaging protocols; or, alternatively, in treatment of a disease associated with specific antigens, i.e. neoplasia and autoimmune disorders.

DETAILED DESCRIPTION OF THE INVENTION INCLUDING PREFERRED EMBODIMENTS

The macrocyclic complexes of this invention are unique in several significant respects. The combination of properties which sets them apart from other complexes of the lanthanide, actinide or yttrium ions includes: kinetic inertness (chemical stabilization) in dilute aqueous solution; high fluorescence excitation efficiency of the europium(III) and terbium(III) derivatives in the presence of suitable enhancers; high relaxivity of the gadolinium(III) complexes; ability to react with, i.e. covalently bond to, biomolecules, i.e. antigens, antibodies, binding proteins etc., either directly or through an intermediate bridging moiety; and relative ease and predictability of synthesis. The conjugation of these complexes to a desired substrate through their pendant functional groups is virtually limitless. Furthermore, such conjugation is effected without adversely altering the fluorescent behavior, relaxivity, or kinetic stability of the complexes in comparison to the non-functionalized analogs.

The complexes of this invention are prepared from starting materials which are either commercially available, or which can themselves be synthesized from commercially available starting materials in accordance with established synthetic procedures or adaptations thereof. As noted above, one of the primary objectives of this invention is to provide a synthetic pathway for the preparation of these complexes, namely, the macrocyclic lanthanide, actinide or yttrium complexes, by the metal templated Schiff-base condensation of (1) a functionalized 1,2-diamine with a 2,6-dicarbonylpyridine, or its furan or thiophene analog, and (2) a functionalized dicarbonylpyridine, furan, or thiophene with 1,2-diaminoethane. The functionalized portion of the diamine or dicarbonyl precursor which does not participate in the Schiff-base condensation reaction, is selected to afford compatibility with subsequent coupling to proteinaceous or polysaccharide materials. The synthesis of these macrocyclic complexes follows established techniques for the lanthanide templated condensation of 2,6-diacetylpyridine or 2,6-diformylpyridine and 1,2-diaminoethane. However, the ability to accomplish such synthesis with a functionalized diamine or dicarbonyl precursor is unique to this process and permits the further coupling of the macrocycle to a biologically compatible synthetic macromolecule, or to what can be collectively classified as a "biomolecule", i.e. cell surface marker, polypeptide or genetic polynucleotide sequence. This coupling is effected through the unreacted coupling functionality of the macrocycle, or through a bridging moiety attached to such coupling functionality.

In one of the preferred embodiments of this invention, the functionalized 1,2-diaminoethane is obtained from a substituted amino acid by the following general reaction scheme. Initially, the substituted amino acid is converted to the corresponding methyl ester hydrochloride by reaction with anhydrous methanol and hydrogen chloride gas. This ester intermediate is further reacted with gaseous ammonia in anhydrous methanol to produce the corresponding amide hydrochloride. The amide hydrochloride is then changed to the free amide by further reaction with ammonia in anhydrous tetrahydrofuran. If necessary, the pendant functional group to be used as a coupling link is protected by the use of one of the many protective groups known in the literature. This protected, free amide is then subjected to reduction with either boron hydride/tetrahydrofuran or lithium aluminum hydride/tetrahydrofuran, followed by acid hydrolysis to produce a functionalized diamine hydrochloride. This diamine hydrochloride is converted to the free diamine by reaction with a base, e.g. sodium methoxide or potassium hydroxide, in anhydrous methanol at 0° C. Substituted amino acids which satisfy the foregoing criteria include, for example: tyrosine, aminophenylalanine, lysine and its analogs, cystine, cysteine, and serine.

In another embodiment of this invention, a functionalized dicarbonyl precursor is prepared from 3-hydroxypyridine by the following scheme. The 3-hydroxypyridine is reacted with formaldehyde (37% in water) in the presence of a strong base (sodium hydroxide, NaOH) at 90° C., to give 3-hydroxy-2,6-bis(hydroxymethyl)pyridine. This is then oxidized with manganese (IV) oxide, in the presence of potassium carbonate (K$_2$CO$_3$). Acidification of the final product gives the hydrochloride of the 2,6-diformylpyridine.

The following structural formulas are representative of some of the materials which are suitable in the preparation of these complexes.

A. Dicarbonyl Reactant

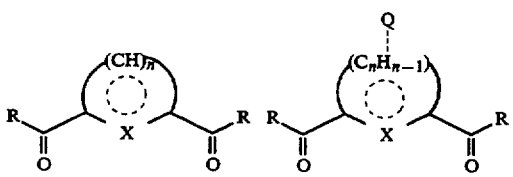

wherein
- n is an integer selected from the group consisting of 2 and 3;
- X is selected from the group consisting of nitrogen, sulfur and oxygen which forms a part of a ring structure selected from the group consisting of pyridine, thiophene or furan, respectively, at the positions marked X;
- R is a substituent selected from the group consisting of hydrogen, methyl, straight-chain or branched alkyl, aryl-substituted alkyl; aryl, and alkyl-substituted aryl, with the proviso that such substituent does not limit the solubility of the resultant complex or otherwise interfere with the cyclization of such complex during its synthesis; and Q is a substituent selected from the group consisting of functionalized methyl, functionalized straight-chain alkyl, functionalized branched-chain alkyl; functionalized aryl-alkyl, functionalized aryl, and functionalized alkyl-aryl: with the proviso that groups of said substituent provide coupling functionality between said substituent and a bridging/linking moiety to permit the derivatization thereof with a receptor molecule or an entity for which there is a corresponding receptor molecule.

The ring structures depicted above specifically include the pyridine, furan and thiophene rings.

B. Metal Ion Salts (M)$_y$(Y)$_m$ wherein
- M is a metal ion selected from the group consisting of a lanthanide having atomic number 57–71, an actinide having atomic number 89–103 and yttrium-(III) having atomic number 39;
- Y is a negatively charged ion, including acetate, carboxylate, sulfonate, halide, nitrate, perchlorate, thiocyanate, and pictate, with the proviso that such negative ion does not limit the solubility of the resultant complex or otherwise interfere with either the coupling procedure or the energy transfer leading to fluorescence;
- m is the ionic charge of the metal ion in the macrocyclic complex; and,
- y is the ionic charge of the counterion in the macrocyclic complex.

C. Diamine Reactant

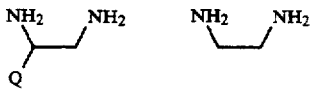

Wherein
- Q is a substituent selected from the group consisting of functionalized methyl, functionalized straight-chain alkyl, functionalized branched-chain alkyl;
- functionalized aryl-alkyl, functionalized aryl, and functionalized alkyl-aryl, with the proviso that groups of said substituent provide coupling functionality between said substituent and a bridging-/linking moiety to permit the derivatization thereof with a receptor molecule or an entity for which there is a corresponding receptor molecule.

The metal templated Schiff-base cyclization involves only one functionalized precursor, either the dicarbonyl compound or the diamine. The functionalized macrocyclic compounds derived from precursors having Q attached to the diamine result in compounds having the structure of Formula I. The functionalized macrocyclic compounds derived from precursors having Q attached to the heterocyclic moiety result in compounds having the structure of Formula II.

An example species of Formula I in which Q is a (4-aminophenyl) methyl group attached to the diamine precursor is represented by the following formula:

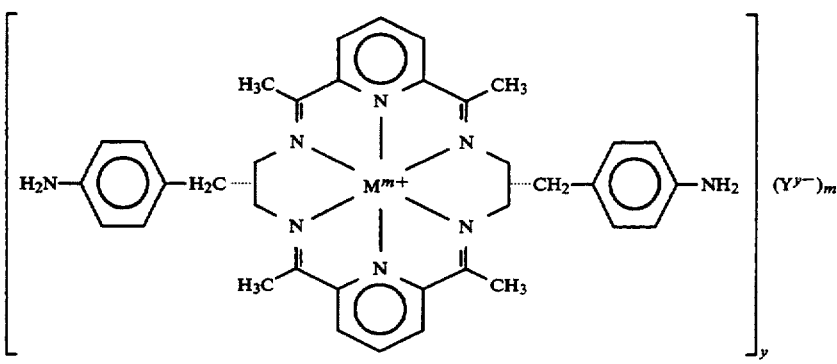

Another example species of Formula I in which Q is a (4-hydroxyphenyl) methyl group attached to the diamine precursor is represented by the following formula:

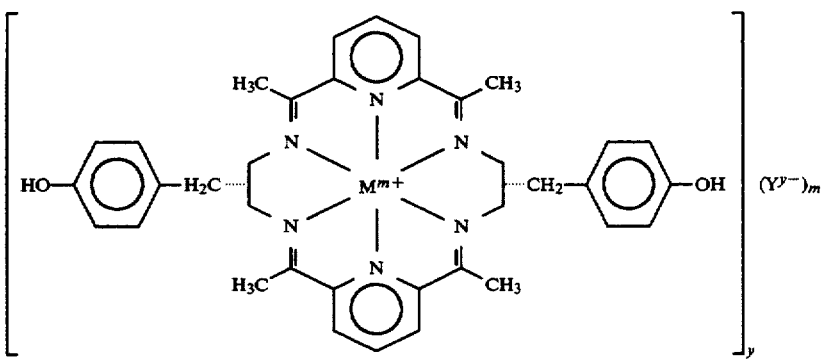

An example species of Formula II in which Q is a hydroxy group attached to the heterocyclic ring of the dicarbonyl precursor is represented by the following formula:

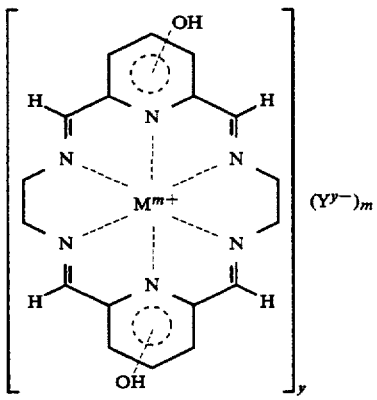

The macrocyclic complexes that have been prepared by this procedure have been isolated as crystalline solids with correct and spectroscopic analysis properties. Most compounds were isolated as solvates.

In order to achieve the desired specific properties, the complexes of this invention are covalently bonded to a reactive substrate, either a biomolecule or a biocompatible natural or synthetic macromolecule which can (1) be targeted for binding only to the analyte of interest and/or, (2) provide reduced tumbling rate in solution for use as MRI contrast agent.

For case (1), the analyte can be any compound of interest for which there exists a complementary binding partner. Such analyte of interest may be either naturally occurring or synthetic and will generally be a compound having physiological activity. These analytes are conveniently grouped by molecular weights. One group of such analytes consists of compounds that have molecular weights in the range of about 125–2,000 daltons and include a wide variety of drugs, small polypeptides, vitamins, enzyme substrates, coenzymes, pesticides, hormones, lipids, etc. The compounds are often referred to "haptens". These compounds include: retinol, vitamin K, cobalamin, biotin, folate, epinephrine, prostaglandins, thyroxine, estrogen, corticosterone, ecdysone, oxytocin, somatostatin, digitoxin, aspirin, penicillin, hydrochlorothiazide, quinidine, and diphenylhydantoin.

Another group of analytes consists of compounds having a molecular weight of 2,000 daltons or more; such as: poly(amino) acids or polypeptides, proteins, polysaccharides, nucleic acids, and combinations thereof, e.g. glycosaminoglycans, glycoproteins, ribosomes, etc. Illustrative compounds include: proteins such as albumins, globulins, hemoglobin, staphylococcal protein A, alpha-fetoprotein, retinol-binding protein, immunoglobulins, avidin, streptavidin, C-reactive protein, collagen, keratin, enzymes, cell surface antigens on T- and B-lymphocytes, i.e. CD-4, and CD-8 proteins, and the rest of the leukocyte cell surface antigens, such as described in the presently employed CD nomenclature; blood group antigens such as A, B and Rh; major histocompatibility antigens both of class 1 and class 2; oncogene products; tumor associated antigens, for instance carcinoembryonic antigen; toxins, such as cholera toxin, diphtheria toxin, and botulinum toxin, snake venom toxins, tetrodotoxin, saxitoxin; lectins, such as concanavalin, wheat germ agglutinin, soy bean agglutinin; polysialic acids, chitin, etc.

The biomolecule to be coupled to the macrocyclic complex for imaging or therapy is typically one selected to carry out a specific target function. In one embodiment, the biomolecule is a monoclonal antibody or antibody fragment which is specific against a selected cell-surface target site. Such antibodies are commercially available, or are made by well-known techniques. Other serum proteins, such as serum albumin are also used advantageously in metal-chelate conjugates for tumor localization and in radioimaging (C. S. H. Leung et al, Int. J. Appl. Rad. Ist., (1978), 29:687).

For the other embodiment, non-targeted nuclear magnetic resonance imaging, the biocompatible macromolecule to be coupled to the macrocyclic complex is typically selected among water-soluble, polymeric compounds of large molecular weight and bulk, known to have slow tumbling rate in aqueous solution at body temperature. Illustrative examples include polysaccharides and polypeptides.

Coupling of the functionalized macrocycle to the desired substrate is accomplished either directly, through linking of the functional group of the macrocycle to an appropriate reactive group of the substrate. Coupling can also be accomplished indirectly, either by the use of a bi-functional cross-linking reagent that provides covalent binding to the substrate, or by binding the macrocycle to another molecule that has a high affinity for the substrate. The affinity binding of biotin with avidin or streptavidin is a well known example, as is goat anti-mouse immunoglobulin with murine monoclonal antibodies.

Direct coupling of the functionalized macrocycle is illustrated by the following formula:

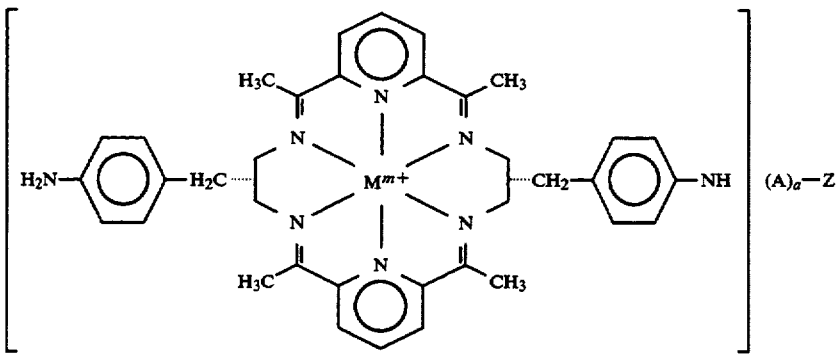

wherein

- A is a linking group between the terminally reactive groups of the macrocyclic complex and a reactive biomolecule, or is a member of a specifically reactive pair;
- a is an integer selected from the group consisting of 0 and 1; and
- Z is a reactive biomolecule, or is a member of a specifically reactive pair.

Serum proteins are directly coupled to the macrocyclic complex through the carboxyl, amine, or thiol groups present on the native protein. For example, an amine-functionalized macrocycle can be directly linked to carboxyl groups in a protein by action of a water soluble carbodiimide to provide a stable cross-linkage. The same reaction in reverse order permits the coupling of a carboxyl-functionalized macrocycle with the free primary amine groups of the protein. A sulfhydryl-functionalized macrocycle can be coupled to proteins containing a free thiol group (cysteine) by mild oxidation to produce stable disulfide linkages. Alternatively, in the case of many proteins including antibody or antibody fragments, free sulfhydryl groups can be generated from disulfide linkages by reduction prior to conjugation, for example, with a sulfhydryl reagent. Nitrous acid treatment of an amino functional group of the macrocyclic complex yields the corresponding diazonium ion, which can react with the tyrosine moieties in proteins and thus provide a link via a diazo bond. The amino group of the macrocycle may also be converted to the corresponding isothiocyanate by treatment with thiophosgene; the isothiocyanate is then reacted directly with proteins for coupling via a thiourea linkage. This coupling method is described in C. F. Meares, et al., *Anal Biochem.* (1984) 142, 68. Yet another reaction involves condensation of a primary amino group with an aldehyde, to produce a Schiff-base linkage. When the functional group of the macrocyclic complex reacts directly with the protein, or with a reduced sulfhydryl group thereof, the length of the macrocycle-protein linker is just that of the functional group of the macrocycle.

Indirect coupling of the functionalized macrocyclic complex to a biomolecule or biologically compatible macromolecule can be achieved by the use of a variety of commercially available cross-linking groups (linkers), see for example, Pierce Handbook and General Catalog, 1988, pages 222-250. When such a cross-linking reagent is used, the length of the macrocycle substrate linker is essentially the length of the cross-linking reagent itself. An example of such usage is described in U.S. Pat. No. 4,678,667 (Example III), which reports a method for coupling the metal-complexing agent p-bromoacetamido-1,4,8,11-tetraaazacyclotetra-decane-N,N',N'',N'''-tetraacetic acid (TETA) to antibody, using the protein-reactive reagent 2-iminothiolane to form a relatively long linker.

In another reaction, the amine functional group of the macrocyclic complex is acylated with a reagent, such as bromoacetylbromide, to form the reactive bromoacetamide group which then readily alkylates free proteins, to form the desired protein/complex conjugate.

Coupling can also occur indirectly when a non-covalent bond is formed between one member of a specific binding pair of interest and the macrocyclic complex. In the case of such indirect techniques, the presence of one of the specific binding pair members of interest is detected by employing an intermediate species, which binds both to that species and the macrocycle. For example, if one wishes to conjugate a macrocyclic complex to avidin, biotin is covalently conjugated to the macrocyclic complex, and the resulting biotinylated macrocyclic complex is combined with avidin; whereby, a macrocyclic complex labeled avidin will result. The reverse coupling of an avidin-bound macrocycle to a biotinated-substrate is equally possible and is indeed advantageous as a variety of biotinated biomolecules are commercially available. This noncovalent coupling can be utilized in yet another way. For example, the macrocycle is covalently coupled to a first antibody, which reacts against a second antibody, which in turn reacts with an analyte of interest. Advantage of the biotin-avidin, or streptavidin-biotin complex can also be taken with either member of this complementary pair being covalently bound to the macrocycle and the other member covalently bound to the antibody.

The macrocyclic complexes of this invention are also reacted with yet another reagent which can mimic, at least immunochemically, an analyte of interest. Depending upon the analyte of interest, a wide variety of functional groups can be employed for conjugating a macrocyclic complex to such other reagent, which will be, for the most part, a low molecular weight compound under 2,000 daltons. The methods for the direct or indirect coupling the macrocyle to such reagent, are in general, those previously outlined for the coupling of the macrocycle to proteins and other substrates.

A principal use of the macrocyclic complexes of this invention is in the field of immunoassay or competitive protein binding assays, where the macrocyclic complexes serve as fluorescent labels (reporter molecules). The macrocyclic complexes which are of particular interest as fluorescent labels contain europium(III) or terbium(III) ions. Each of these macrocyclic complexes absorbs excitation energies in the range of 280–360 nm. The emissions are quite narrow, half-band width, approximately 4 nm and occur in the visible range of the electromagnetic spectrum. The most intense emissions are at approximately 615 nm and 680 nm for europium-(III) and at approximately 545 nm for terbium(III). The preferred macrocyclic complexes are used in conjunction with certain sensitizers to enhance the fluorescence intensity. For example, it is possible to enhance the photoresponsiveness of the Eu(III) macrocyclic complex by substitution of the acetate ions, which are associated with the complex, by the anions of 1,3-diphenyl-propane-1,3-dione (dibenzoylmethane), 4,4,4-trifluoro-1(2-thienyl)butane-1,3-dione, 2-picolinic, 2-furoic, or 2-thiophenic acid. For the Tb(III) macrocyclic complex, fluorescence enhancement has been obtained by substitution of the acetates with acetylacetonate and its fluoro-derivatives. The pendant functional groups of the macrocycle permit conjugation of the fluorescent structure to an analyte, analyte mimic or a receptor (an antibody). While for the most part the antibodies of choice will be an IgG fraction, other antibodies such as IgA, IgD, IgE and IgM can also be appropriate, depending upon the objective of the assay. In addition, various naturally occurring receptors can be employed; particularly, receptors having high binding specificity, such as avidin. By biotinylating either the receptor or the macrocyclic complex, a wide variety of molecules can be linked through avidin. The resultant conjugate can be utilized in any one of a variety of fluorescent assays.

The paramagnetism of the lanthanides with electron configurations $4f^1$ to $4f^{13}$ and in particular of gadolinium(III) ($4f^7$) is well known to affect the relaxation time of the protons of water in nuclear magnetic resonance experiments. This effect has been used in the past to enhance the sensitivity of in vivo nuclear magnetic resonance imaging; see for example the references cited in U.S. Pat. No. 4,678,667, at column 1, lines 12–68. The macrocyclic complexes of this invention possess, in aqueous media, at least three fast exchanging water molecules in direct contact with the paramagnetic center and thus provide an intrinsic sensitivity as MRI contrast agents that far exceeds that of compounds used for this purpose in the past, such as the salts of the gadolinium(III)-triethylenediamine pentaacetic acid complex. Furthermore, the slowing of solution tumbling rate that results from the binding of the functionalized macrocycle to a biomolecule or biocompatible macromolecule, specifically a linear or cross-linked polysaccharide, provides major additional sensitivity enhancement.

The conjugatable macrocyclic structures also include radioactive isotopes of the ions of the 5f-block elements, including transuranium elements, as well as of yttrium-(III). The radioactive emissions from these elements include: alpha particles, fission fragments, beta rays, positrons and gamma rays. Specific killing of neoplastic or other selected cells is achieved by bringing these radioactive elements in proximity to these cells via a macrocyclic structure coupled to an appropriate targeting biomolecule.

If the radioactivity is long range, such as strong gamma rays, the metal-macrocycles can also be used as reporter groups for imaging.

SUMMARY OF SPECIAL FEATURES OF FUNCTIONALIZED MACROCYCLIC COMPLEXES

As noted previously, the macrocyclic complexes of this invention are unique in that they are soluble in a wide variety of aqueous solvents, mixtures of water, water compatible solvents such as dioxane, tetrahydrofuran, dimethylsulfoxide, and lower alkyl alcohols, as well as most non-aqueous organic solvents, except diethylether or hydrocarbons. These macrocyclic entities further possess excellent kinetic stability, in that they do not dissociate in dilute aqueous solution, nor do they release the lanthanide, actinide, or yttrium ions, even in the presence of acids, bases or competing ligands. When intense fluorescence is desired, the complexes can be combined with certain enhancers to maximize excitation and energy transfer to the fluorochrome ion and to provide an added degree of protection against quenching by the solvent. Finally, the functionality provided by one of their formative reactants affords the additional capability of derivatization of the macrocycle with any appropriate natural or synthetic substrate, such as an analyte mimic or receptor, a linear or branched polysaccharide, or a preformed functionalized polymer. For macrocyclic complexes that exhibit metal-ion fluorescence, this derivatization can be accomplished without materially altering the efficiency of absorption of the activating electromagnetic radiation and/or the transfer of energy from the absorbing species to the lanthanide ion of the complex. For the gadolinium(III) macrocycles intended for use as magnetic resonance contrast agents, the derivatization with large molecular weight water-compatible substrates actually enhances the relaxivity by slowing down the tumbling rate of the paramagnetic species in solution.

The following examples are provided to further illustrate the synthesis, characterization and use of the macrocyclic complexes of this invention. Apparatus and equipment employed in the synthesis, characterization and evaluation of these macrocyclic complexes is standard, or as hereinbefore described. Parts and percentages appearing in such examples are by mass, unless otherwise indicated.

EXAMPLE I

Synthesis of a Functionalized Hexz-Aza-Macrocylic Complex of Europium(III) Acetate Having Pendant(4-Hydroxyphenyl)Methyl Groups

A. MATERIALS (a) Hydrated europium acetate (white, non-hygroscopic crystals), commercially available from Alpha-Thiokol, Catalog No. 15307 (1986–87);

(b) 2,6-Diacetylpyridine (white, crystalline powder), commercially available from Aldrich Chemical Co., Catalog No. D880-1 (1987), and, (c) Tyrosine amide (white, crystalline powder), commercially available from Sigma Chemical Co., Catalog No. 3879 (1987).

B. PROCEDURE

1Preparation of 1,2-diamino-3-(4-hydroxyphenyl)propane (Tyrosine Diamine)

Preliminary to the preparation of the macrocyclic complex, the tyrosine amide was converted to the corresponding diamine hydrochloride, following a slight modification of the procedure described by Meares et al. (C. F. Meares et al., *Anal. Biochem.*, 1984 142, 68). This conversion involved the following procedure, which was carried out in a non-oxidizing atmosphere, using, as solvent, a mixture of tetrahydrofuran (THF) and 1,2-dimethoxyethane.

Solid tyrosine amide (1.5 g, 8.3 mmol) was added to a reaction vessel containing a solvent mixture consisting of 300 mL of anhydrous 1,2-dimethoxyethane (Gold-Label Grade from Aldrich Chemical Co.) and 100 mL of anhydrous THF (Gold-Label Grade from Aldrich Chemical Co.) under nitrogen. The resultant solution was chilled in an ice bath and 75 mL of 0.10M solution of boron hydride ($BH_3$) in THF were introduced with a syringe through a rubber septum into the reaction vessel. The $BH_3$ solution was added over a period of thirty (30) minutes with constant stirring of the contents of the vessel. During this period, a white fluffy solid formed, which precipitated from the reaction medium. The reaction was allowed to continue by refluxing the contents of the reaction vessel for an additional six (6) hours. The contents of the reaction vessel were cooled and then chilled in an ice bath for about thirty (30) minutes. One hundred (100) mL of anhydrous methanol were added to the reaction vessel and the white fluffy precipitate dissolved. The clear solution thus obtained was saturated with HCl gas and refluxed for one (1) hour, resulting in the crystallization of a first crop of the desired diamine dihydrochloride. The solid was filtered and the mother liquor was evaporated to dryness in a rotary evaporator under reduced pressure. Recrystallization of the solid residue produced another crop of the white crystalline dihydrochloride. Total yield was approximately 65%. Microanalysis and spectral data (IR, UV, $^1H$ and $^{13}C$ NMR) confirmed both the structure and purity of the product as the diamine dihydrochloride.

The free-base diamine was prepared in the following manner: 1.00 g (4.2 mmol) of the dihydrochloride was suspended in 15 mL of anhydrous THF, and about 10 mL of a methanol solution of sodium methoxide (0.46 g, 8.5 mmol) were added with constant stirring. The mixture was refluxed and stirred for one (1) hour, with stirring continued for an additional hour upon cessation of heating. The mixture was then placed in a refrigerator at 0° C. overnight. During this heating and cooling process, a white precipitate formed (sodium chloride), which was removed by filtration and discarded. The filtrate, a clear yellow solution, was diluted to a total volume of 50 mL with anhydrous methanol, placed in a tightly stoppered bottle, and stored under refrigeration. This solution, containing the tyrosine diamine (0.084 mol/L), had a limited shelf life and, thus, was freshly prepared prior to its use in the synthesis of the macrocyclic complex.

2. Preparation of the Europium(III) Acetate Macrocyclic Complex

Europium(III) acetate (0.18 g, 0.50 mmol), 2,6-diacetylpyridine, (0.163 g, 1.0 mmol) and 20 mL of anhydrous methanol were placed in a flask and flushed with a slow and continuous stream of nitrogen. The mixture was heated to a temperature of 60° C. and 1 mmol (11.9 mL of the solution from step 1 of this example) of tyrosine diamine dissolved in anhydrous methanol was introduced into the flask by dropwise addition. The contents of the flask immediately turned bright yellow. The mixture was heated under reflux conditions for twelve (12) hours in a nitrogen atmosphere and progressively changed from cloudy to clear. The flask was then placed in a rotary evaporator and the yellow-amber solution was evaporated, under reduced pressure, to an amber, oily residue. The crude macrocyclic complex was obtained from this residue by repeated work-up with anhydrous diethylether. The product was purified by dissolving it in a minimal volume of methanol, filtering off any undissolved residue, and re-precipitating by addition of diethylether at 0° C. The product was isolated as off-white microcrystals, yield approximately 60%. It was very soluble in polar organic solvents and moderately soluble in water. Mass spectral analysis as well as IR and NMR spectra ($^1H$ and $^{13}C$) of the purified material were consistent with the assigned structure.

The europium(III) macrocyclic complex, obtained as described above, exhibited fluorescence upon ultraviolet irradiation in methanol solution. Since the pattern of the emission spectrum was characteristic of europium(III) in a hexa-aza-macrocyclic environment, (N. Sabbatini, L. De Cola, L. M. Vallarino, G. Blasse, *J. Phys. Chem*, 1987, 91, 4681–4685, Radiative and Nonradiative Transitions in the Eu(III) Hexa-aza Macrocyclic Complex [(Eu($C_{22}H_{26}N_6$)($CH_3COO$)]($CH_3COO$)Cl.2$H_2O$), this observation provided additional confirmation as to the structure of the europium macrocyclic entity. The intrinsic fluorescence intensity of this europium macrocycle entity was relatively low, but could be enhanced substantially when the macrocyclic complex was combined with certain coordinating anions (enhancers). For example, substitution of the acetate ions by the anions of 2-furoic acid, 2-thiophenic acids, or 1,3-diphenylpropane-1,3-dione, produced a pale yellow solution that exhibited intense europium macrocyclic fluorescence. A marked increase of fluorescence intensity in the presence of these enhancers has been reported for non-functionalized hexa-aza macrocyclic complexes of europium(III) (L. De Cola, D. L. Smailes, L. M. Vallarino, Proceedings of X Convegno Nazionale Di Fotochimica, Ravenna, Italy, 1985, p.4, Effect of Heteroligands on the Luminescence Properties of Cationic Macrocyclic Complexes and Tb(III).)

EXAMPLE II

Synthesis of a Functionalized Hexa-Aza-Macrocylic Complex of Terbium(III) Acetate Having Pendant (4-Hydroxyphenyl)Methyl Groups The procedures of Example I were repeated with the substitution of terbium(III) acetate for europium(III) acetate. The infrared spectrum of the purified material confirmed the composition of the hexa-aza-macrocyclic complex of terbium(III) acetate.

EXAMPLE III Synthesis of a Functionalized Hexa-Aza-Macrocyclic Complex of Lanthanum(III) Acetate Having Pendant (4-Hydroxyphenyl)Methyl Groups The procedures of Example I were repeated with the substitution of lanthanum(III) acetate for europium(III) acetate. The IR and NMR ($^1H$ and $^{13}C$) spectra of the product were consistent with the assigned macrocyclic structure.

EXAMPLE IV

Synthesis of a Functionalized Hexa-Aza-Macrocyclic Complex of Yttrium(III) Acetate Having Pendant (4-Hydroxyphenyl)Methyl Groups The procedures of Example I were repeated with the substitution of yttrium(III) acetate for europium(III) acetate. The IR and NMR ($^1$H and $^{13}$C) spectra of the product were consistent with the assigned macrocyclic structure.

EXAMPLE V

Synthesis of Functionalized Hexa-Aza-Macrocyclic Complexes of the Uranyl Ion Having Pendant (4-hydroxyphenyl)Methyl Groups The procedures of Example I were repeated with the substitution of uranyl ($UO_2^{++}$) acetate for europium-(III) acetate. The macrocyclic uranyl complexes were then isolated as the nitrate, perchlorate, or thiocyanate salts by exchange of the original acetates with $NO_3^-$, $ClO_4^-$, or $SCN^-$ counterions, respectively. Infrared spectra of the purified materials confirmed their structure as hexa-aza-macrocyclic complexes of the uranyl ion.

EXAMPLE VI

Synthesis of a Functionalized Hexa-Aza-Macrocyclic Complex of Lanthanum(III) Acetate Having Pendant (4-Aminoxyphenyl)Methyl Groups

A. MATERIALS (a) Hydrated lanthanum acetate (white, crystalline solid), commercially available from Aldrich Chemical Company, Catalog No. 30633-9;

(b) 2,6-Diacetylpyridine available from Aldrich Chemical Company Catalog No. D880-1(1987); and, (c) 4-Aminophenylalanine (white, crystalline solid), commercially available from Aldrich Chemical Company, Catalog No. 85,870-6.

B. PROCEDURE

1. Preparation of 1,2-diamino-3-(4-aminopenyl)propane

Preliminary to the preparation of the lanthanum(III) macrocyclic complex, the 4-aminophenylalanine was converted to the corresponding triamine trihydrochloride. This conversion involved the following four-step procedure:

1.1 Solid 4-aminophenylalanine (1.00 g, 5.55 mmol) was suspended in 25 mL of anhydrous methanol and stirred at room temperature for 15 minutes. A brisk stream of anhydrous HCl gas was bubbled through the suspension, thereby causing the suspended matter to dissolve, forming a pale yellow solution. After refluxing for 30 minutes, the solution was taken to dryness in a rotary evaporator under reduced pressure. The cream colored powder thus formed was recrystallized from methanol-diethylether. Microanalysis of this product (C,H,N), as well as IR and NMR spectra ($^1$H and $^{13}$C) confirmed its composition to be the methyl ester dihydrochloride of 4-aminophenylalanine.

1.2 The methyl ester dihydrochloride of 4-aminophenylalanine was converted to the corresponding amide dihydrochloride as follows: A stream of anhydrous gaseous ammonia was bubbled through a solution of the methyl ester (1.00 g, 3.74 mmol) in anhydrous methanol (40 mL) chilled at 0° C., the flask was then stoppered tightly, and the mixture was allowed to stand 4 hours at room temperature. The procedure was repeated 4–5 times. The resulting clear pale yellow solution was evaporated to dryness in a rotary evaporator under reduced pressure. The pale yellow solid residue was shown by its infrared spectrum to be the hydrochloride of the amide, containing a small amount of ammonium chloride. Recrystallization from methanol-diethylether gave the pure product as white crystals with correct C, H, N microanalysis, as well as IR and NMR spectra ($^1$H and $^{13}$C).

1.3 The amide dihydrochloride was converted to the "free base" amide as follows: The solid dihydrochloride (1.00 g, 4.64 mmol) was ground to a fine powder and suspended in anhydrous tetrahydrofuran (THF) (150 mL) in a moisture-protected vessel. A stream of anhydrous gaseous ammonia was bubbled through the stirred suspension for 10 minutes at room temperature, and then for 5 minutes at 45° C. During this procedure, the solution turned yellow and the appearance of the suspended solid changed. The mixture was chilled in a refrigerator for 1 hour and then filtered; the solid was submitted twice to the THF/ammonia treatment and the final residue (ammonium chloride) was discarded. The combined filtered THF solutions were evaporated to dryness under reduced pressure, to produce the amide as a fluffy off-white powder, which was dried over phosphorus pentoxide. The product discolored upon prolonged exposure to air. Microanalysis (C,H,N) and spectra (IR, $^1$H and $^{13}$C NMR) confirmed the structure of the compound. Total yield, approximately 80% based on 4-aminophenylalanine.

1.4 The amide of 4-aminophenylalanine was converted to the corresponding triamine trihydrochloride by the following procedure which was carried out under a stream of dry nitrogen gas.

The solid amide (2.50 g, 13.9 mmol) was placed in a 500 mL round-bottom three-neck flask equipped with reflux condenser with drying tube protection, dry nitrogen gas inlet, and septum stopper. (Prior to adding the amide, the flask was heated with a flame under a dry nitrogen stream, and allowed to cool under nitrogen). To the amide, 140 ml of 1,2-dimethoxyethane (anhydrous, Gold Label grade from Aldrich Chemical Company) and 50 ml of THF (anhydrous, Gold-Label grade from Aldrich Chem Co.) were added with a syringe through the rubber septum. The mixture was stirred and chilled at 0° C. for 15 minutes. A solution of borane ($BH_3$) in THF (70 mL, 1.0M, Aldrich Chemical Co.) was slowly added to the chilled and stirred mixture which was further stirred at 0° C. for 15 minutes. The rubber septum was replaced by a Teflon stopper and the contents of the vessel were refluxed for 5 hours. The resulting slightly cloudy, colorless mixture was chilled at 0° C., and 50 mL of anhydrous methanol were added very slowly. Brisk evolution of gas was observed at first and the solution became clear. The solution was then saturated with HCl gas and a white precipitate formed. Water circulation in the reflux condenser was discontinued, the drying tube was removed, and the solution was heated to boiling for 1 hour in a brisk stream of nitrogen, thus reducing the volume to approximately one-half. After cooling, the white precipitate was filtered off with suction, washed with anhydrous THF and dried in a vacuum desiccator over phosphorous pentoxide. Yield 70%. The product had microanalysis (C,H,N) corresponding to the trihydrate of the triamine trihydrochloride; IR and NMR spectra ($^1$H and $^{13}$C) confirmed the assigned structure.

2. Preparation of the Lanthanum(III) Acetate Macrocyclic Complex.

The triamine trihydrochloride of 4-aminophenylalanine (0.188 g, 0.65 mmol) was dissolved in 15 mL of anhydrous methanol, and solid potassium hydroxide (0.89 g, 0.44 mmol), was added to the solution. The resultant suspension was stirred at room temperature for 1 hour, and thereafter refrigerated overnight. The suspension was filtered, the solid (potassium chloride) was discarded, and the clear pale yellow filtrate was added dropwise, with stirring, to a reaction vessel containing lanthanum(III) acetate hydrate (0.110 g, 0.32 mmol) in 40 mL of anhydrous methanol. The resultant mixture was stirred at room temperature for 15 min and then 2,6-diacetylpyridine (0,104 g, 0.65 mmol) was added. The mixture was heated under reflux conditions for 14 hours; the orange colored solution thereby produced was filtered to remove a small amount of unreacted europium acetate and evaporated to dryness under reduced pressure at 60° C. in a rotary evaporator. The gummy residue was repeatedly worked up in diethyl ether, ultimately yielding a solid product. This solid was taken up in warm chloroform and filtered. The insoluble residue was discarded, and the yellow-orange filtrate was gradually diluted with diethylether and chilled. The precipitate thus formed was filtered, dissolved in anhydrous methanol, and added dropwise with stirring to approximately 300 mL of chilled anhydrous diethylether. The pale yellow powdery solid thus formed was filtered off, washed with diethylether, and dried in vacuo over phosphorous pentoxide. Yield: 58%. Microanalysis and spectral data (IR, $^1$H and $^{13}$C NMR) confirmed the structure and purity of the product.

EXAMPLE VII

Synthesis of a Functionalized Hexa-Aza-Macrocyclic Complex of Lanthanum(III) Thiocyanate Having Pendant (4-Aminophenyl)Methyl Groups The thiocyanate salt of the macrocyclic complex cation of Example VI was prepared by treating a sample of the corresponding acetate macrocycle with an excess of sodium thiocyanate, both reagents being dissolved in a small volume of methanol. After the initial formation of a cloudy dispersion, a microcrystalline, yellow-orange solid separated slowly. This was filtered off, washed exhaustively with methanol, and dried in vacuo over phosphorus pentoxide. The microanalysis (C,H,N) and IR spectrum showed this product to be the anhydrous triisothiocyanate of the macrocyclic complex.

EXAMPLE VIII

Synthesis of a Functionalized Hexa-Aza-Macrocyclic Complex of Europium(III) Acetate Having Pendant (4-Aminophenyl)Methyl Groups The procedure of Example VI was repeated with the substitution of europium(III) acetate for lanthanum(III) acetate; the europium complex was obtained as a light yellow powder. The microanalysis (C,H,N) and infrared spectrum showed this product to be the triacetate of the europium(III) macrocycle.

EXAMPLE IX

Synthesis of a Functionalized Hexa-Aza-macrocyclic Complex of Europium(III) Thiocyanate Having Pendant (4-Aminophenyl)Methyl Groups The europium(III) macrocyclic acetate of Example VIII was transformed to the corresponding thiocyanate salt by the procedures given in Example VII. The microanalysis (C,H,N) and infrared spectrum of the product were consistent with the anhydrous triisothiocyanate of the europium(III) macrocycle.

EXAMPLE X

Synthesis of a Functionalized Hexa-Aza-Macrocyclic Complex of Gadolinium(III) Acetate Having Pendant (4-Aminophenyl)Methyl Groups The procedure of Example VI was repeated with the substitution of gadolinium(III) acetate for lanthanum(III) acetate. The microanalysis (C,H,N) and infrared spectrum of this product were consistent with the triacetate of the gadolinium(III) macrocycle.

EXAMPLE XI

Synthesis of a Functionalized Hexa-Aza-Macrocyclic Complex of Terbium(III) Acetate Having Pendant (4-Aminophenyl)Methyl Groups The procedures of Example VI were repeated with the substitution of terbium(III) acetate for lanthanum(III) acetate. The microanalysis (C,H,N) and infrared spectrum of the product were consistent with the triacetate of the terbium(III) macrocycle.

EXAMPLE XII

Synthesis of a Functionalized Hexa-Aza-Macrocyclic Complex of Yttrium(III) Acetate Having Pendant (4-Aminophenyl)Methyl Groups The procedures of Example VI were repeated with the substitution of yttrium(III) acetate for lanthanum(III) acetate. The microanalysis (C,H,N) and spectra (IR, $^1$H and $^{13}$C NMR) of the product were consistent with the triacetate of the yttrium(III) macrocycle.

EXAMPLE XIII

Synthesis of a Functionalized Hexa-Aza-Macrocyclic Complex Of Yttrium(III) Thiocyanate Having Pendant (4-Aminophenyl)Methyl Groups The yttrium(III) macrocyclic acetate of Example XII was transformed to the corresponding thiocyanate by the procedures given in Example VII. The microanalysis (C,H,N) and infrared spectrum of the product were consistent with the anhydrous triisothiocyanate of the yttrium(III) macrocycle.

EXAMPLE XIV

Synthesis of a Functionlized Hexa-Aza-Macrocyclic Complex of Lanthanum(III) Acetate Having Pendant Hydroxymethyl Groups

A. MATERIALS (a) Hydrated lanthanum(III) acetate, commercially available from Aldrich Chemical Co., catalog No. 30633-9;

(b) 2,6-Diacetylpyridine, available from Aldrich Chemical Co., Catalog No. D880-1(1987); and (c) Serine amide hydrochloride monohydrate, (white, crystalline solid), available from Sigma Chemical Co., catalog No. 34750.

B. PROCEDURE

1. Preparation of 2,3-diaminopropan-1-ol dihydrochloride

This compound was prepared from serine amide hydrochloride monohydrate by first changing the hydrochloride to the free-base amide, following the procedure described in Example VI, Section B.3. The free-base amide was then reduced by the procedure described in Example I, Section B.1. The final white crystalline product had microanalysis (C,H,N) and IR spectrum consistent with 2,3-diaminopropanol dihydrochloride. Yield: 85%. Immediately before use in the synthesis of the macrocycle, the free base diamine was obtained by the procedure described in Example I, Section B.1.

2. Preparation of the Lanthanum(III) Acetate Macrocyclic Complex

This compound was obtained and purified by the procedure described in Example I, Section 2, with the substitution of 2,3-diaminopropan-1-ol for 1,2-diamino-3-(4-hydroxyphenyl)propane, and of lanthanum(III) acetate for europium(III) acetate. The product was obtained as a white crystalline powder; its microanalysis (C,H,N) and spectra (IR, $^1H$ and $^{13}C$ NMR) were consistent with the triacetate of the lanthanum(III) macrocycle.

EXAMPLE XV

Synthesis of a Functionalized Hexa-Aza-Macrocylic Complex of Europium(III) Acetate Having Pendant Hydroxymethyl Groups This complex was obtained as described in Example XIV, Section B.2, with the substitution of europium(III) acetate for lanthanum(III) acetate. The microanalysis (C,H,N) and infrared spectrum of the product were consistent with the triacetate of the europium(III) macrocycle.

EXAMPLE XVI

Fluorescence Enhancement of the Hexa-Aza-Macrocyclic Complex of Europium(III) Acetate Having Pendant (4-Aminophenyl)Methyl Groups

A. MATERIALS (a) Europium(III) acetate macrocyclic complex of Example VIII.

(b) Freshly prepared sodium salt of 1,3-diphenylpropane-1,3-dione (dibenzoylmethane, HDBM), the latter available from Aldrich Chemical Co., Catalog No. D3,345-4.

(c) 4,4,4-Trifluoro-1-(2-thienyl)butane-1,3-dione (thenoyltrifluoroacetylacetone, THTFAcAc, white crystalline solid), available from Aldrich Chemical Co., Catalog No. T2,700-6.

B. PROCEDURE

1. Preparation of the Sodium Salt of 1,3-Diphenylpropane-1,3-dione (NaDBM) Solid HDBM (0.223 g, 1.0 mmol) was added to a solution prepared by dissolving clean sodium metal (0.023 g, 1.0 mmol) in anhydrous methanol (50 mL). The mixture was stirred at 50° C. for 30 minutes, and then evaporated to dryness under reduced pressure in a rotary evaporator, to yield silky pale yellow needles of sodium 1,3-diphenylpropane-1,3-dionate. Yield: 100%.

2. Fluorescence Titration of the Europium Macrocycle with NaDBM

A series of seven solutions was prepared, containing a constant concentration ($1.0 \times 10^{-4}M$) of the europium(III) acetate macrocycle of Example VIII and regularly increasing concentrations of the enhancer, the sodium salt of dibenzoylmethane (NaDBM), ($0.50 \times 10^{-4}M$, $1.5 \times 10^{-4}M$, $2.0 \times 10^{-4}M$, $2.5 \times 10^{-4}M$, $3.0 \times 10^{-4}M$, $3.5 \times 10^{-4}M$). In each case the solvent was a mixture of dioxane and distilled water (2:8 volume ratio). The fluorescence emission spectrum of each solution was measured at room temperature, with excitation at 370 nm. The intensity of the (red) emission of the europium macrocycle at 615 nm was observed to increase markedly as the mole ratio of NaDBM to europium macrocycle increased, reaching a maximum for a 2.5:1.0 (approximate) mole ratio.

3. Isolation of the Europium(III) Macrocycle-DBM Complex

The europium(III) macrocycle of Example VIII (0.875 g, 1.00 mmol) and NaDBM (0.452 g, 2.00 mmol) were separately dissolved in chloroform (20 mL each) and the two solutions were mixed with stirring. The mixture was warmed at 50° C. for 5 minutes and the resulting turbid yellow suspension was filtered. The solid was discarded and the clear yellow solution was evaporated to a total of 5 mL under reduced pressure in a rotary evaporator. Dilution with 50 mL of anhydrous diethylether and chilling at 0° C. for one hour promoted the precipitation of a cream-colored granular solid (yield, 60%) which exhibited intense fluorescence at 615 nm when excited at 370 nm. The IR spectrum of the product was consistent with its formulation as the acetate-DBM complex of the europium(III) macrocycle.

4. Fluorescence Titration of the Europium(III) Macrocycle with THTFAcAc

The procedures described in Section B.2 of this Example were repeated with the substitution of 4,4,4-trifluoro-1-(2-thienyl)butane-1,3-dione (thenoyltrifluoroacetylacetone, THTFAcAc) for NaDBM. A maximum of fluorescence enhancement was observed for a 1.0:3.0 (approximate) mole ratio of europium(III) macrocycle to HTHTFAcAc.

EXAMPLE XVII

Fluorescence Enhancement of the Hexa-Aza-Macrocyclic Complex of Europium(III) Acetate Having Pendant (4-Hydroxyphenyl)Methyl Groups The procedures described in Example XVI, Sections B.2 and B.4, were repeated with the substitution of the europium(III) macrocyclic complex of Example I for the europium(III) macrocyclic complex of Example VIII. In each case a marked enhancement in fluorescence emission at 615 nm, with excitation at 370 mm, was observed for a 1.0:2.5 (approximate) mole ratio of europium(III) macrocycle to enhancer.

EXAMPLE XVIII

Synthesis of a Functionalized Hexa-Aza-Macrocyclic Complex of Lanthanum(III) Having Pendant Hydroxy groups

A. MATERIALS (a) 3-Hydroxypyridine, solid, m.p. 126–129, commercially available from Aldrich Chemical Co., Catalog No. 19,3-406 (1989).

(b) Formaldehyde 37% aqueous solution, A.C.S. Reagent Grade, commercially available from Aldrich Chemical Co., Catalog No. 25,254-9 (1989).

(c) Ethylenediamine (1,2-diaminoethane) dihydrochloride, white crystalline solid, commercially available from Aldrich Chemical Co., Catalog No. 19, 580-4 (1989).

(d) Manganese(IV) dioxide, Activated, black powder, commercially available from Aldrich Chemical Co., Catalog No. 21, 764-6 (1989).

(e) Succinic anhydride, m.p. 119°–120° C., Gold Label grade, commercially available from Aldrich Chemical Co., Catalog No. 23, 969-0.

(f) Lanthanum(III) acetate hydrated, white crystalline powder, commercially available from Aldrich Chemical Company, Catalog No. 30633-9.

B. PROCEDURES

1. Preparation of 3-Hydroxypyridine-2,6-dialdehyde

Preliminary to the synthesis of the macrocyclic complex, 3-hydroxypyridine is converted to the corresponding 2,6-dialdehyde by a modification of the method of M. A. Baldo et al. (M. A. Baldo, G. Chessa, G. Marangoni, and B. Pitteri, *Synthesis*. 720,1987). The procedure consists of the following two steps:

1.1 Preparation of 3-hydroxy-2,6-bis(hydroxmethyl)-pyridine

3-Hydroxy-pyridine (23.8 g, 0.25 mol) and solid sodium hydroxide (NaOH, 10.0 g, 0.25 mol) are dissolved in water (100 mL) and the solution is heated to 90° C. To this hot stirred solution, a 37% aqueous solution of formaldehyde (85mL) is added dropwise over a period of eight (8) hours. After the addition of formaldehyde is completed, the mixture is stirred at 90° C. for an additional 90 minutes. Heating is then discontinued and the mixture is chilled at 0° C., neutralized by the addition of 15 mL of acetic acid ($CH_3COOH$), and evaporated to dryness in a rotary evaporator under reduced pressure. The residue is taken up in 200 mL of dimethylformamide, filtered to remove any undissolved solid which is discarded, and acidified by the addition of concentrated aqueous hydrochloric acid (25 mL). The acidified solution is evaporated to dryness in a rotary evaporator under reduced pressure and the residue is dissolved in methanol (150 mL), clarified with activated charcoal, and filtered. The resulting clear solution is again evaporated to dryness in a rotary evaporator under reduced pressure. Recrystallization of the oily residue, first from n-propanol and then from methanol-acetone, yields the desired product (yields, 35%) as a cream-colored solid, m.p. 144° C, having the correct analytical and spectral (IR and NMR) properties.

1.2 Preparation of 3-Hydroxy-2,6-diformylpyridine

The 3-hydroxy-2,6-bis(hydroxymethyl)pyridine prepared in the preceding step (5.00 g, 26 mmol) is dissolved in anhydrous ethanol (100 mL) and to this solution 3.58 g (26 mmol) of anhydrous potassium carbonate ($K_2CO_3$) are added at room temperature. After stirring for five (5) hours at room temperature, the suspension is filtered, the solid is discarded, and the clear filtrate is evaporated to dryness in a rotary evaporator under reduced pressure. The oily residue is dissolved in 150 ml of methanol-acetone (20–80 mixture) and solid activated manganese (IV) oxide ($MnO_2$, 35 g) is added. The suspension is stirred at room temperature for seven days, after which time it is filtered over Celite, discarding the solid portion. The solution is evaporated to dryness under reduced pressure at room temperature and the residue is dried under vacuum for two days, in the presence of solid potassium hydroxide and Drierite. The solid thus obtained is used directly in the synthesis of the lanthanum(III) macrocycle. Identification of the product is obtained from IR and NMR spectra, without recrystallization to prevent air-decomposition.

2. Preparation of Lanthanum(III) Acetate Macrocyclic Complex

A mixture of ethylenediamine dihydrochloride (1.33 g, 10 mmol) and solid potassium hydroxide (0.56 g, 10 mmol) is stirred at room temperature for 30 minutes and then chilled at 0° C. for one hour. The solid that forms is filtered off and discarded; the filtered solution is placed in a flask equipped with reflux condenser and nitrogen gas inlet. Solid lanthanum(III) acetate hydrate (1.58 g, 5 mmol) is added and the mixture is stirred and warmed at 40° C. for 30 minutes. After this time, 3-hydroxy-2,6-diformylpyridine (1.51 g, 10 mmol) dissolved in anhydrous methanol (50 mL) is added dropwise and with stirring over a period of 15 minutes. The resulting cloudy yellow suspension is refluxed for six (6) hours under a slow nitrogen stream; the nitrogen flow is then discontinued and the mixture is allowed to cool to room temperature and filtered, discarding the solid residue. The clear yellow solution is evaporated to dryness in a rotary evaporator under reduced pressure, to yield a yellow solid which is recrystallized several times from methanol-diethylether. Characterization of the lanthanide macrocycle with pendant hydroxy groups is obtained from chemical analysis and from IR and NMR spectra.

EXAMPLE XIX

Synthesis of a Functionalized Hexa-Aza-Macrocyclic Complex of Lanthanum(III) Having Pendant Carboxylic Acid Groups Conversion of the 3-hydroxypyridine-lanthanum-macrocycle-to the Succinic Acid Monoester A sample (0.67 g, 1.0 mmol) of the 3-hydroxypyridine-lanthanum macrocycle obtained in step B.2 of Example XVIII is placed in 100 mL of chloroform and succinic anhydride (0.200 g, 2.0 mmol) dissolved in 50 mL of chloroform is added dropwise and with stirring. The mixture is refluxed for four (4) hours, filtered to remove any suspended solid, and evaporated to dryness in a rotary evaporator under reduced pressure. The residue is crystallized several times from methanol-diethylether.

Characterization of the lanthanum(III) macrocycle with pendant carboxylic acid groups is obtained from chemical analysis (C,H,N) and spectra (IR and NMR).

EXAMPLE XX

Synthesis of a Functionalized Hexa-Aza Macrocyclic Complex of Europium(III) having Pendant Carboxylic Acid Groups The procedures of Example XIX are repeated with the substitution of europium(III) acetate for lanthanum-(III) acetate. Microanalysis (C,H,N) as well as IR spectra confirm the formula and purity of the product.

EXAMPLE XXI

Fluorescence Enhancement of the Hexa-Aza Macrocyclic Complex of Europium(III) Having Pendant Carboxylic Acid Groups The procedures of Example XVI are repeated with the substitution of the europium-macrocycle of Example XX for the europium(III) macrocycle of Example VIII. The maximum fluorescence intensity at 615 nm is observed for a 1:2 molar ratio of macrocycle to enhancer, with excitation at 370 nm.

EXAMPLE XXII

Coupling of the Hexa-Aza-Macrocyclic Complex of Europium(III) Acetate Having Pendant (4-Aminophenyl)Methyl Groups to Streptavidin Using N-Succinimidyl 3-(2-Pyridyldithio) Propionate (SPDP)

A. MATERIALS (a) N-Succinimidyl 3-(2-pyridyldithio)propionate, SPDP, commercially available from Pierce Chemical Co., Catalog No. 21557;

(b) D,L-Dithiothreitol, DTT, commercially available from Sigma Chemical Co., Catalog No. D-0632;

(c) Sodium carbonate buffer, 0.1M, pH 8–8.2;

(d) Phosphate Buffered Saline, PBS, commercially available from Sigma Chemical Co., Catalog No. 1000-3;

(e) Methanol Spectranalyzed, commercially available from Fisher Scientific Catalog No. A408-4;

(f) BioGel P-6 ion exchange resin column 200–400 mesh, 1 cm×30 cm, commercially available from BioRad Catalog No. 1500750;

(g) 4,4,4-Trifluoro-1-(2-thienyl)butane-1-3-dione (thenoyltrifluoroacetylacetone, THTFAcAc), available from Aldrich Chemical Co., Catalog No. T2,700-6.

PROCEDURE

The biotin binding equivalent weight of Streptavidin (SA) was calculated to be 16,267 a.m.u. from the stated maximum biotin binding activity, 15 micrograms per mg of protein, and the molecular weight of biotin, 244 a.m.u. On this basis, the equivalent weight of the SPDP cross-linker (molecular weight 312 a.m.u.) was calculated to be 19 micrograms per mg of SA.

One vial of Streptavidin (Zymed 43-4301, lot #80401000, 1 mg per vial lyophilized from 1 mL of SA in PBS) was reconstituted with 1 mL of water and the solution was quantitatively transferred to a second vial of SA to achieve a concentration of 123 nmol SA per mL. Fifty-eight microliters of a 2 g/L (372 nmoles) SPDP solution in methanol was added and swirled to mix. The solution was allowed to stand at room temperature for one hour to accomplish conjugation of SPDP to SA. Fifty (50) microliters of 0.1M DTT in water were added and the resulting mixture was let stand for 30 min to reduce the —S—S— bond of SPDP forming —SH. The thiol-substituted-SA was purified by passage over a BioGel P6 column which had previously been equilibrated with PBS. One (1) mL fractions were collected. The thiol-SA eluted between 4 to 7 mL of effluent, while the unreacted SPDP and DTT and their low molecular weight reaction products eluted at fractions 8 to 10. The SA-containing fractions were pooled. The column was regenerated by flowing fifty (50) mL of PBS through it.

A sample (0.0062 g, 6.4 micromoles) of the p-aminophenyl-substituted europium(III) macrocyclic complex of Example VIII was dissolved in 1.5 mL of sodium carbonate buffer, pH 8 to 8.2, to give a 4 mM solution, and 0.0667 mL of the 2 g/L solution of SPDP (6.4 micromole) were added. This mixture was allowed to stand for about one hour to achieve conjugation.

A sample (0.186 mL, 377 nmole) of the SPDP-p-aminophenyl-europium(III) macrocycle reaction mixture was added to the thiol-substituted-SA chromatogram pool and the resulting solution was allowed to stand for about 30 min to achieve conjugation.

The reaction mixture was desalted over a BioGel P6 column, as before. The front-eluting fractions, containing the p-aminophenyl-europium(III) macrocycle-Streptavidin conjugate were pooled. Care was taken to exclude the late-eluting, low molecular weight reactants.

The presence of the labeled streptavidin was detected by adding a few drops of a concentrated solution of the THTFAcAc enhancer and observing the red fluorescence induced by a mercury 355 nm ultraviolet lamp.

EXAMPLE XXIII

Coupling of the Hexa-Aza-Macrocyclic Complex of Europium(III) Acetate Having Pendant (4-Aminophenyl)Methyl Groups to an Antibody Using Glutaraldehyde The derivatization, or conjugation, of the europium-(III) macrocyclic complex of Example VIII with an antibody specific for T-cell surface markers (Coulter T4 cell marker, Catalog No. 4235131, available from Coulter Immunology Division, Hialeah, Fla.) is achieved by combining the complex and the antibody in aqueous-organic solution containing glutaraldehyde at neutral pH. The resulting conjugate is useful in immunoassay and in flow cytometric analysis involving time resolved fluorescence monitoring techniques.

EXAMPLE XXIV

Coupling of the Hexa-Aza-Macrocyclic Complex of Europium(III) Acetate Having Pendant (4-Aminophenyl)Methyl Groups to an Antibody Using Sulfsuccinimidyl(4-Iodoacetyl)Aminobenzoate (Sulfo-SIAB)

The derivatization, or conjugation of the macrocyclic complex of Example VIII with an antibody specific for a T-cell marker (Coulter T4 cell specific antibody, Catalog No. 4235131, available from Coulter Immunology Division, Hialeah, Fla. ) is achieved by combining the complex and the antibody in an aqueous-organic solution containing sulfsuccinimidyl(4-iodoacetyl)aminobenzoate (sulfo-SIAB), in accord with the procedures described by J. K. Weltman et al, *Bio Techniques* 1, 148–152 (1983). The resulting conjugate is useful in immunoassay and in flow cytometric analysis employing time resolved fluorescence monitoring techniques.

EXAMPLE XXV

Use of the Europium(III) Acetate Macrocylic Complex Having Pendant (4-Aminophenyl)Methyl Groups As Imminological Stains for Flow Cytometry 1. Evaluation Procedure The europium(III) macrocyclic complex of Example VIII which is coupled to an antibody by the procedures described in Examples XXII, XXIII, and XXIV is employed as an immunological stain for surface markers on T cells found in whole blood. This use involves the use of the COULTER ® Q-PREP automated staining-/sample preparation equipment developed by Coulter Electronics, Inc. (Hialeah, Fla.). This process initially involves the placement of the appropriate lyric reagent system, stain and fixative on the Q-PREP instrument, placement of the whole blood sample in a chamber (test tube) within the instrument, and thereafter directing the apparatus to execute one of two available processing sequences.

2. Reagents (a) The lytic reagent system used in this evaluation comprises a dilute aqueous solution of formic acid (0.5% v/v) and a companion salt solution which rapidly and effectively retards the lyric action of the formic acid, while at the same time restoring the salt balance of pH of the sample to its physiological state and contains the enhancer, THTFAcAc of Example XVI;

(b) The fixative is paraformaldehyde.

3. Flow Cytometric Analysis

After the sample has been prepared on the Q-PREP mixer/staining equipment, the test tube containing the staining/sample preparation equipment is transferred to an EPICS ® IV flow cytometer and subjected to analysis in accordance with the standard flow cytometric analytical procedures. The scattergram produced thereby provides good differentiation between the macrocyclic complex labeled cells and the other constituents of the sample. The resultant scattergram permits ready differentiation of the macrocomplex labeled cells from the non-labeled cells, thus, confirming the kinetic stability of such derivatized complexes in dilute aqueous solution and the retention of the fluorescent properties of the complex even after derivatization.

EXAMPLE XXVI

Use of the Europium(III) Acetate Macrocyclic Complex Having Pendant (4-Aminophenyl)Methyl Groups as Immunological Stains for Fluorescene Microscopy Human leukocytes are prepared from peripheral blood by layering over a Ficol-Pague solution of density 1.077 g/mL and removing the top layer after unit gravity sedimentation. 100 microliters of these cells are diluted with 180 microliters phosphate buffered saline and labelled with 20 microliters (25 test vial) biotinylated T8 COULTER CLONE ® monoclonal antibody for 30 minutes at 25° C. A microscope slide pretreated with poly-1-lysine, 1 g/L, is mounted in a Centrifugal Cytology Bucket Coulter part number 7787046. 200 microliters of ISOTON ® III diluent and 100 microliters of the labeled cells are each inserted into a sample block chamber. A dispersion of these cells is prepared by centrifuging at 500 RPM (radius 6.5 in) for 5 minutes at 25° C. The supernatant is withdrawn, the bucket disassembled and the slides are immersed in fixative (acetone:formaldehyde:acetic acid, 85:10:5) for 30 minutes before rapid air drying using a heat gun (Master number 0388). The cellular DNA is stained by immersing the slides in a staining solution which contains $2.5 \times 10^{-5}$ g of DAPI (Sigma Chemical Co., Catalog No. D-1388) per ml of PBS. The cells are labelled with the p-aminophenyl-europium(III) macrocycle-SA conjugate from Example XVIII. The preparation is mounted in glycerol containing 4,4,4-trifluoro-1-(2-thienyl)butane-1,3-dione, which acts as an enhancer and is observed with an epiilluminated microscope employing ultraviolet light excitation at 350–385 nm. The lymphocyte nuclei are blue-green and the T8 lymphocytes have a red periphery.

EXAMPLE XXVII

Use of the Europium(III) Acetate Macrocyclic Complex Having pendant (4-Aminophenyl)Methyl Groups as Reporter Molecules for Solid Phase Immunoassays 1. Preparation of microtiter wells Twelve (12) well strips (Polystyrene white microtiter wells, MicroFluor; Dynatech Laboratories, Alexandria, Va. 22314) are coated for 18–20 hours at 4° C. with, per well, 200 ng (100 microliters) of purified monoclonal anti-AFP antibody (Medix Biotech Inc., Foster City, Calif. 94404; Catalog No. A-013-01) dissolved in 50 mmol/L carbonate buffer, pH 9.6. The wells are manually washed twice with the wash solution, consisting of 9 g/L NaCl solution containing 0.5 mL of polyoxyethylene sorbitan monolaurate (Tween 20) per liter. A blocking solution consisting of 0.1 mol/L sodium bicarbonate buffer (pH 8.3) containing 10 g of bovine serum albumin (RIA grade; Sigma Chemical Co.), 20 g of sucrose, and 0.5 g of sodium azide per liter, is added (200 microliter/well) and allowed to react for 1 hour at room temperature. The wells are washed again with washing solution. They are stored dry at 4° C., and are stable for several weeks.

Biotinylation of antibody

Affinity-purified goat anti-AFP polyclonal antibody (Atlantic Antibodies, Scarborough, Me. 04074; cat co. 077-06) is dialyzed twice against 5 L of isotonic saline (NaCl 9 g/L) and then is diluted with carbonate buffer (0.1 mol/L, pH 9.0) to give a final concentration of 0.50 g/L. To 1 mL of this solution is added a 500-fold molar excess of sulfosuccinimidyl-6-(biotinamido)hexanoate ("NHS-LC-biotin"; Pierce Chemical Co.) which is dissolved in 100 microliter of dimethyl sulfoxide, and the mixture is incubated for 1 hour at room temperature. The reaction mixture is then dialyzed twice at 40° C. against 5 L of 0.1 mmol/L bicarbonate buffer (pH 8.3) containing 0.25 g of sodium azide per liter.

Before use the biotinylated antibody solution is diluted 300-fold in 10 mmol/L Tris HCl buffer (pH 7.8) containing, per liter, 400 mmol of KCl, 10 g of bovine serum albumin, 0.1 g of sodium azide, and 0.1 g of thimerosal.

Preparation of labeled streptavidin

The europium(III)-macrocycle-streptavidin conjugate of Example XXII is diluted before use in 50 mmol/L Tris HCl buffer (pH 7.8), containing, per liter, 10 g of bovine serum albumin, 9 g of NaCl, 0.1 g of sodium azide, and 0.1 g of thimerosal to give a final concentration of 10 micromoles/L.

AFP standards

Human AFP (InterMedico, Toronto, Canada) is calibrated against the international reference standard (72/227) for AFP. AFP standards are prepared in concentrations ranging from 1 to 1000 micrograms/L in the standards-diluent solution.

Immunoassay procedure

Twenty (20) microliters of standards or samples are added to each well, then 100 microliter of standards-diluent buffer (10 mmol/L phosphate buffer (pH 7.0), containing 10 mmol of EDTA, 50 g of the albumin, 0.1 g of sodium azide, and 0.1 g of thimerosal per liter are added. The wells are incubated for 45 min at 37° C. (air oven). This is followed by washing the wells twice with the wash solution. The 300-fold-diluted biotinylated anti-AFP antibody solution (100 microliter/well) is added; the wells are incubated for another 45 minutes at 37° C., then the wells are washed as above. One-hundred (100) microliter per well of the europium(III)-macrocycle-streptavidin complex working solution are added, and the wells are incubated for an additional 30 minutes at 37° C. The wells are washed as above and 100 microliters of 1 micromolar solution of the enhancer THTFAcAc are added. The fluorescence of each well is measured using a CyberFluor 615 time-resolved fluorometer/analyzer, using an excitation wavelength of 337.1 nm (nitrogen laser source) and an emission wavelength of 615 ($\pm$5)nm (interference filter).

Specimens of serum from pregnant women at various gestational ages, amniotic fluids, and serum from patients with liver-and testicular-tumors are used. Human sera-based "Tri-level" ligand controls are obtained from Ortho pharmaceuticals, Raritan N.J. The amniotic fluid is diluted 50-fold in the standards-diluent solution before analysis.

The kinetic stability of the macrocyclic complexes of this invention is unique. Thus, their use in analytical, therapeutic and imaging applications sets them apart from materials presently available and disclosed in the prior art.

The foregoing description has been provided as illustrative of some of the preferred embodiments of this invention- It is not intended, however, as delimiting the scope thereof, which is defined in the claims which are presented hereinafter.

The embodiments of the invention in which an exclusive property or privilege is claimed are defined as follows:

1. A method for the preparation of functionalized hexa-donor-macrocyclic complexes, said method comprising:

(a) combining in a common reaction vessel a metal salt and appropriate dicarbonyl and diamine precursors, in the following combinations:

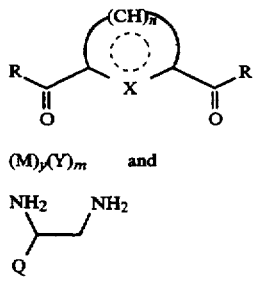

(1)

$(M)_y(Y)_m$ and (2)

NH$_2$ NH$_2$ (3)

wherein

M is a metal ion selected from the group consisting of a lanthanide having atomic number 57–71, an actinide having atomic number 89–103 and yttrium-(III) having atomic number 39;

R is a substituent selected from the group consisting of hydrogen, methyl, straight-chain and branched alkyl, aryl-substituted alkyl, aryl, and alkyl-substituted aryl, with the proviso that such substituent does not limit the solubility of the resultant complex or otherwise interfere with the cyclization of such complex during its synthesis;

X is selected from the group consisting of nitrogen, sulfur and oxygen which forms a part of a ring structure selected from the group consisting of pyridine, thiophene or furan, respectively, at the positions marked X;

Q is a substituent selected from the group consisting of functionalized straight-chain alkyl, functionalized branched-chain alkyl; functionalized aryl-alkyl, functionalized aryl, and functionalized alkylaryl; with the proviso that groups of said substituent provide coupling functionality between said substituent and a bridging/linking moiety to permit the derivatization thereof with a receptor molecule or an entity for which there is a corresponding receptor molecule;

n is an integer selected from the group consisting of 2 and 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex; and y is the ionic charge of the counterion in the macrocyclic complex; and (b) reacting the foregoing compounds under conditions to effect a Schiff-base cyclic, metal templated condensation of the dicarbonyl and diamine compounds, so as to form a coordination complex with the metal ion.

2. A method for the preparation of functionalized hexa-donor-macrocyclic complexes, said method comprising:

(a) combining in a common reaction vessel a metal salt and appropriate dicarbonyl and diamine precursors, in the following combinations:

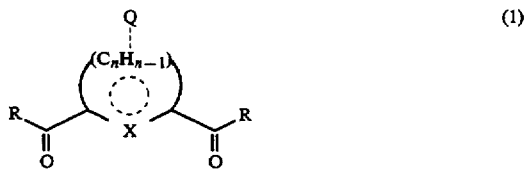

(1)

$(M)_y(Y)_m$ and (2)

NH$_2$ NH$_2$ (3)

wherein

M is a metal ion selected from the group consisting of a lanthanide having atomic number 57–71, an actinide having atomic number 89–103 and yttrium-(III) having atomic number 39;

R is a substituent selected from the group consisting of hydrogen, methyl, straight-chain and branched alkyl, aryl-substituted alkyl, aryl, and alkyl-substituted aryl, with the proviso that such substituent does not limit the solubility of the resultant complex or otherwise interfere with the cyclization of such complex during its synthesis;

X is selected from the group consisting of nitrogen, sulfur and oxygen which forms a part of a ring structure selected from the group consisting of pyridine, thiophene or furan, respectively, at the positions marked X;

Q is a substituent selected from the group consisting of functionalized methyl, functionalized straight-chain alkyl, functionalized branched-chain alkyl; functionalized aryl-alkyl, functionalized aryl, and functionalized alkyl-aryl; with the proviso that groups of said substituent provide coupling functionality between said substituent and a bridging-/linking moiety to permit the derivatization thereof with a receptor molecule or an entity for which there is a corresponding receptor molecule;

n is an integer selected from the group consisting of 2 and 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex; and y is the ionic charge of the counterion in the macrocyclic complex; and (b) reacting the foregoing compounds under conditions to effect a Schiff-base cyclic, metal templated condensation of the dicarbonyl and diamine compounds, so as to form a coordination complex with the metal ion.

3. A method of preparation of functionalized hexadonor-macrocyclic complexes, said process comprising:

(a) combining the following compounds in common reaction vessel:

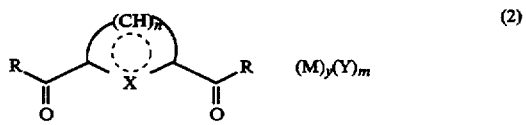

(2)

and

(3)

wherein

R is a substituent selected from the group consisting of hydrogen; straight chain or branched alkyl; aryl substituted alkyl; aryl; and alkyl substituted aryl, with the proviso that such substituent does not limit the solubility of the resultant complex or otherwise interfere with the cyclization of such complex during its synthesis;

M is a metal ion of the lanthanide or actinide series, or yttrium(III);

X is nitrogen, sulfur or oxygen;

Q is a substituent selected from the group consisting of substituted alkyl; substituted aryl; and substituted aralkyl, with the proviso that groups of said substituent provide coupling functionality between said substituent and a bridging/linking moiety to permit the derivatization thereof with a receptor molecule or an entity for which there is a corresponding receptor molecule; and n is 2 or 3;

Y is any suitable negatively charged ion, such as carboxylate, halide, nitrate, thiocyanate, with the proviso that such negative ion does not limit the solubility of the resultant complex or interfere with the either the coupling procedure or the energy transfer leading to fluorescence;

m is the ionic charge, or valence, of the metal ion in the macrocyclic complex; and, y is the ionic charge, or valence, of the counterion in the macrocyclic complex (b) reacting the foregoing compounds under conditions to effect a Schiff-base cyclic, metal templated, condensation of the dicarbonyl and diamine compounds, so as to form a coordination complex with the metal ion.

4. Compounds of the formula

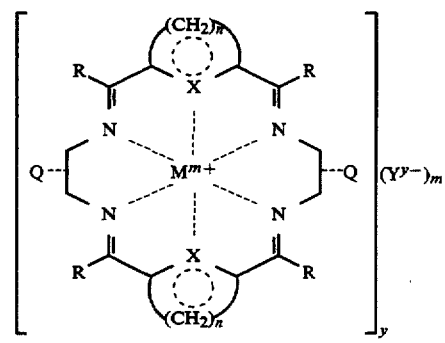

wherein

R is a substituent selected from the group consisting of hydrogen, straight-chain alkyl, branched-chain alkyl, aryl-substituted alkyl, aryl, and alkyl-substituted aryl, with the proviso that such substituent does not limit the solubility of the resultant complex or otherwise interfere with the cyclization of such complex during its synthesis;

M is a metal ion selected from the group consisting of a lanthanide having atomic number 57–71, an actinide having atomic number 89–103 and yttrium-(III) having atomic number 39;

X is selected from the group consisting of nitrogen, sulfur and oxygen which forms a part of a ring structure selected from the group consisting of pyridine, thiophene or furan, respectively, at the positions marked X;

Q is a substituent selected from the group consisting of functionalized straight-chain alkyl, functionalized branched-chain alkyl; functionalized aryl-alkyl, functionalized aryl, and functionalized alkyl-aryl, with the proviso that groups of said substituent provide coupling functionality between said substituent and a bridging/linking moiety to permit the derivatization thereof with a receptor molecule or an entity for which there is a corresponding receptor molecule;

n is an integer selected from the group consisting of 2 and 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex; and y is the ionic charge of the counterion in the macrocyclic complex.

5. Conjugates of the compounds of claim 4, comprising a macrocyclic complex with a linking group, said conjugates having the following formula

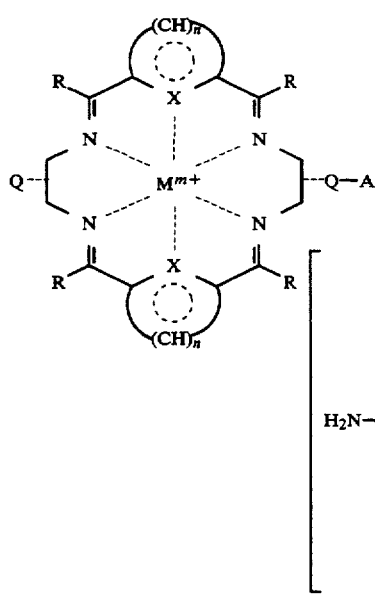

wherein

A is a linking group between the terminally reactive groups of the macrocyclic complex and a reactive biomolecule or a member of a specifically reactive pair.

6. The conjugates of claim 5, having the formula

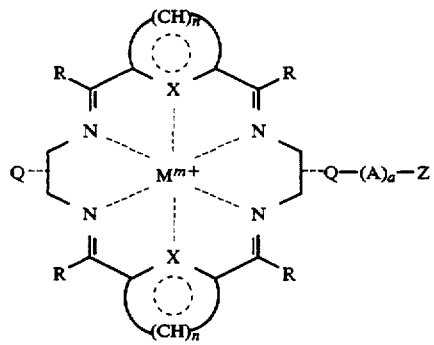

wherein

Z is a reactive biomolecule, or is a member of a specifically reactive pair; and a is an integer selected from the group consisting of 0 and 1.

7. The compounds of claim 4 having the formula:

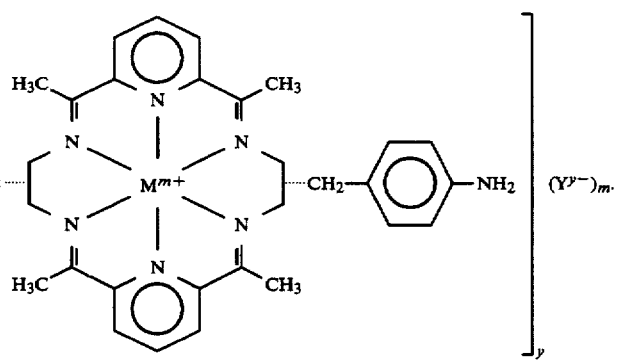

8. Conjugates of the compounds of claim 7, comprising a macrocyclic complex with a linking group, said conjugates having the following formula

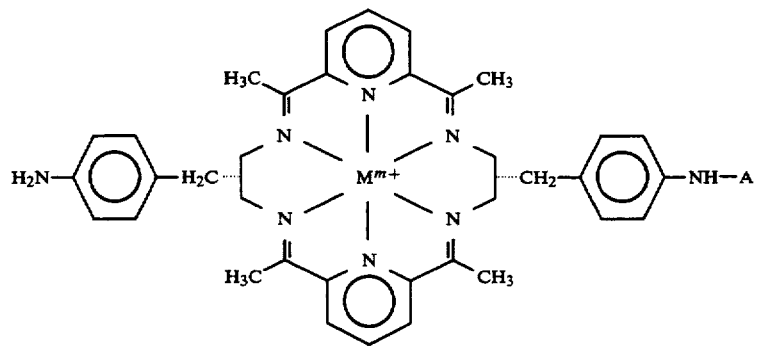

wherein

A is a linking group between the terminally reactive groups of the macrocyclic complex and a reactive biomolecule or a member of a specifically reactive pair.

9. The conjugates of claim 8, having the formula

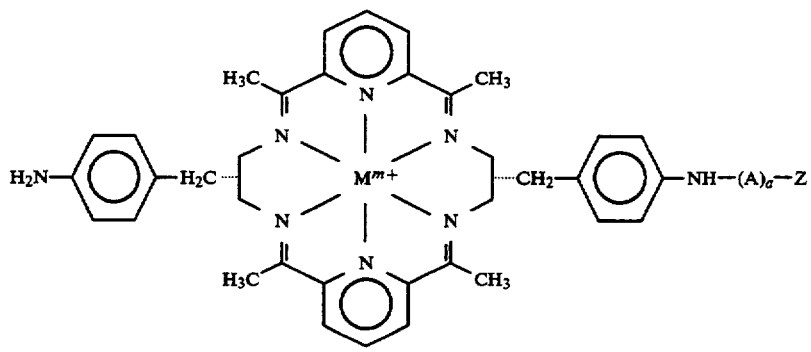

wherein
Z is a reactive biomolecule, or is a member of a specifically reactive pair; and
a is an integer selected from the group consisting of 0 and 1.

10. The functionalized hexa-aza-macrocyclic complex having pendant (4-aminophenyl)methyl groups of claim 7 with lanthanum(III) acetate.

11. The functionalized hexa-aza-macrocyclic complex having pendant (4-aminophenyl)methyl groups of claim 7 with lanthanum(III) thiocyanate.

12. The functionalized hexa-aza-macrocyclic complex having pendant (4-aminophenyl)methyl groups of claim 7 with europium(III) thiocyanate.

13. The functionalized hexa-aza-macrocyclic complex having pendant (4-aminophenyl)methyl groups of claim 7 with gadolinium(III) thiocyanate.

14. The functionalized hexa-aza-macrocyclic complex having pendant (4-aminophenyl)methyl groups of claim 7 with terbium(III) acetate.

15. The functionalized hexa-aza-macrocyclic complex having pendant (4-aminophenyl)methyl groups of claim 7 with yttrium(III) acetate.

16. The functionalized hexa-aza-macrocyclic complex having pendant (4-aminophenyl)methyl groups of claim 7 with yttrium(III) thiocyanate.

17. The functionalized hexa-aza-macrocyclic complex having pendant (4-aminophenyl)methyl groups of claim 7 with europium(III) acetate 18. The compounds of claim 4 of the formula:

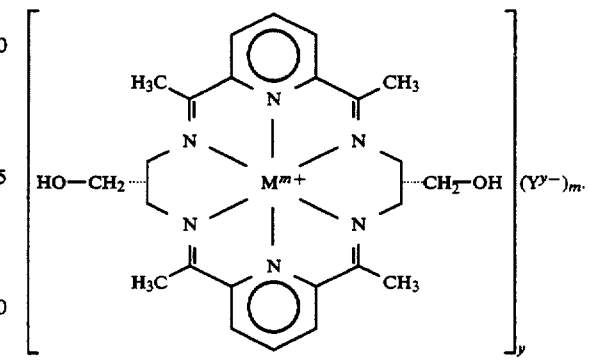

19. The functionalized hexa-aza-macrocyclic complex having pendant hydroxymethyl groups of claim 18 with lanthanum(III) acetate.

20. The functionalized hexa-aza-macrocyclic complex having pendant hydroxymethyl groups of claim 18 with europium(III) acetate.

21. The compounds of claim 4 of the formula

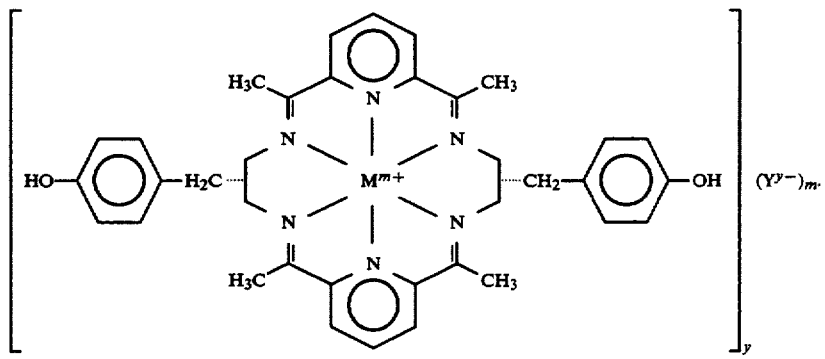

22. The functionalized hexa-aza-macrocyclic complex having pendant (4-hydroxyphenyl)methyl groups of claim 21 with terbium(III) acetate.

23. The functionalized hexa-aza-macrocyclic complex having pendant (4-hydroxyphenyl)methyl groups of claim 21 with lanthanum(III) acetate.

24. The functionalized hexa-aza-macrocyclic complex having pendant (4-hydroxyphenyl)methyl groups of claim 21 with yttrium(III) acetate.

25. The functionalized hexa-aza-macrocyclic complexes having pendant (4-hydroxyphenyl)methyl groups of claim 21 with the uranyl ion.

26. The functionalized hexa-aza-macrocyclic complex having pendant(4-hydroxyphenyl)methyl groups of claim 21 with europium(III) acetate.

27. Compounds of the formula

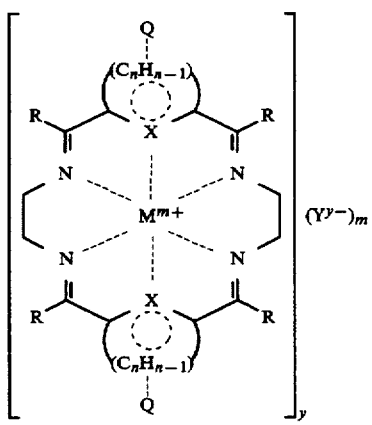

wherein

- R is a substituent selected from the group consisting of hydrogen, straight-chain alkyl, branched-chain alkyl, aryl-substituted alkyl, aryl, and alkyl-substituted aryl, with the proviso that such substituent does not limit the solubility of the resultant complex or otherwise interfere with the cyclization of such complex during its synthesis;
- M is a metal ion selected from the group consisting of a lanthanide having atomic number 57–71, an actinide having atomic number 89–103 and yttrium-(III) having atomic number 39;
- X is selected from the group consisting of nitrogen, sulfur and oxygen which forms a part of a ring structure selected from the group consisting of pyridine, thiophene or furan, respectively, at the positions marked X;
- Q is a substituent selected from the group consisting of functionalized methyl, functionalized straight-chain alkyl, functionalized branched-chain alkyl; functionalized aryl-alkyl, functionalized aryl, and functionalized alkyl-aryl, with the proviso that groups of said substituent provide coupling functionality between said substituent and a bridging-/linking moiety to permit the derivatization thereof with a receptor molecule or an entity for which there is a corresponding receptor molecule;
- n is an integer selected from the group consisting of 2 and 3;
- Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;
- m is the ionic charge of the metal ion in the macrocyclic complex; and
- y is the ionic charge of the counterion in the macrocyclic complex.

28. Conjugates of the compounds of claim 27 comprising a macrocyclic complex with a linking group, said conjugates having the following formula

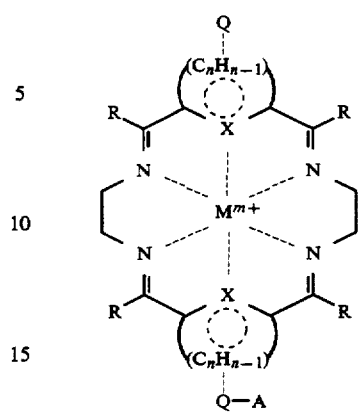

wherein

- A is a linking group between the terminally reactive groups of the macrocyclic complex and a reactive biomolecule or a member of a specifically reactive pair.

29. The conjugates of claim 28, having the formula

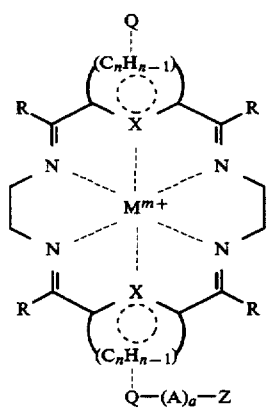

wherein

- Z is a reactive biomolecule, or is a member of a specifically reactive pair; and
- a is an integer selected from the group consisting of 0 and 1.

30. The compounds of the formula

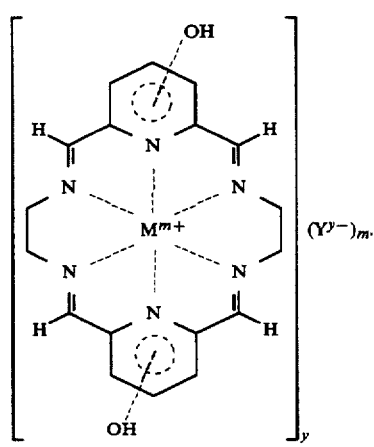

31. The functionalized hexa-aza-macrocyclic complex of the compounds of claim 30 with lanthanum(III) acetate.

32. The functionalized hexa-aza-macrocyclic complex of lanthanum(III) having pendant carboxylic acid groups of claim 31.

33. The functionalized hexa-aza-macrocyclic complex of europium(III) having pendant carboxylic acid groups of claim 30.

34. A compound of the formula

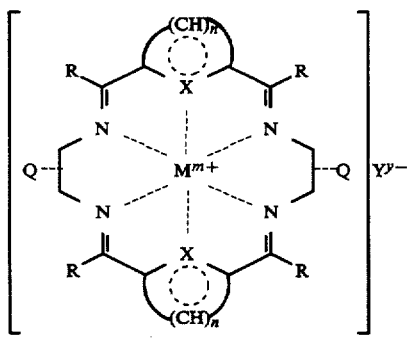

wherein
R is a substituent selected from the group consisting of hydrogen; straight chain or branched alkyl; aryl substituted alkyl; aryl; and alkyl substituted aryl, with the proviso that such substituent does not limit the solubility of the resultant complex or otherwise interfere with the cyclization of such complex during its synthesis;

M is a metal ion of the lanthanide or actinide series, or yttrium (III);

X is nitrogen, sulfur or oxygen;

Q is a substituent selected from the group consisting of substituted alkyl; substituted aryl; and substituted aralkyl, with the proviso that groups of said substituent provide coupling functionality between said substituent and a bridging/linking moiety to permit the derivatization thereof with a receptor molecule or an entity for which there is a corresponding receptor molecule;

n is 2 or 3;

Y is any suitable negatively charged ion, such as carboxylate, halide, nitrate, thiocyanate; with the proviso that such negative ion does not limit the solubility of the resultant complex or interfere with the either the coupling procedure or the energy transfer leading to fluorescence;

m is the ionic charge, or valence, of the metal ion in the macrocyclic complex; and, y is the ionic charge, or valence, of the counterion in the macrocyclic complex.

35. The compound of claim 34 of the formula:

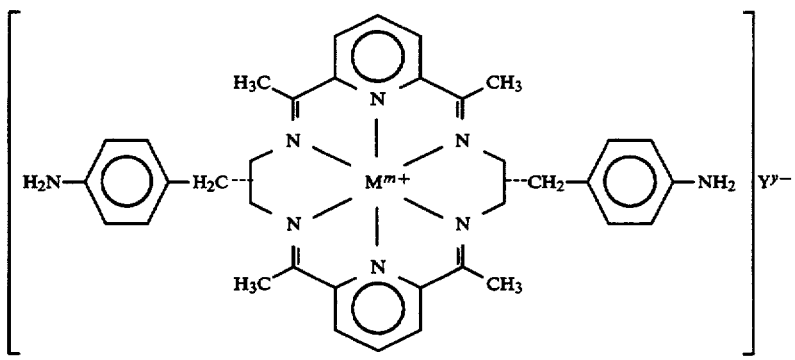

wherein
Y is a suitable negatively charged ion comprising carboxylate, halide, nitrate, or thiocyanate, with the proviso that such negative ion does not limit the solubility of the resultant complex or interfere with either the coupling procedure or the energy transfer leading to fluorescence, and y is the ionic charge or valence of the counterion in the macrocyclic complex.

36. A conjugate comprising a macrocyclic complex linked to a biomolecule, said conjugate having the following formula:

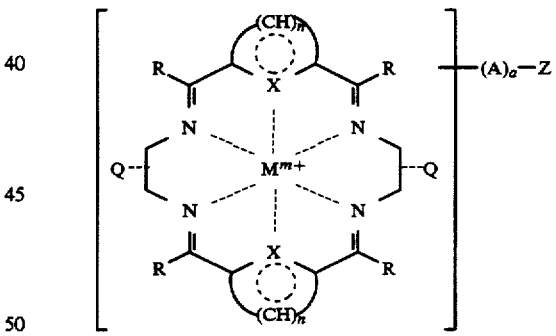

wherein
R is a substituent selected from the group consisting of hydrogen; straight chain or branched alkyl; aryl substituted alkyl; aryl; and alkyl substituted aryl, with the proviso that such substituent does not limit the solubility of the resultant complex or otherwise interfere with the cyclization of such complex during its synthesis;

M is a metal ion of the lanthanide or actinide series;

X is nitrogen, sulfur or oxygen;

Q is a substituent selected from the group consisting of substituted alkyl; substituted aryl; and substituted aralkyl, with the proviso that groups of said substituent provide coupling functionality between said substituent and a bridging/linking moiety to permit the derivatization thereof with a receptor molecule or an entity for which there is a corresponding receptor molecule;

n is 2 or 3;

Y is a suitable negatively charged ion comprising carboxylate, halide, nitrate, thiocyanate, with the proviso that such negative ion does not limit the solubility of the resultant complex or interfere with the either the coupling procedure or the energy transfer leading to fluorescence;

m is the ionic charge, or valence, of the metal ion in the macrocyclic complex;

y is the ionic charge, or valence, of the counterion in the macrocyclic complex;

A is a linking group between the terminally reactive groups of the macrocyclic complex and a reactive biomolecule;

Z is a reactive biomolecule which is either specific for binding to an analyte of interest or mimics functionally characteristic groups of an analyte of interest; and, a is 0 or 1.

37. The conjugate of claim 36 of the formula,

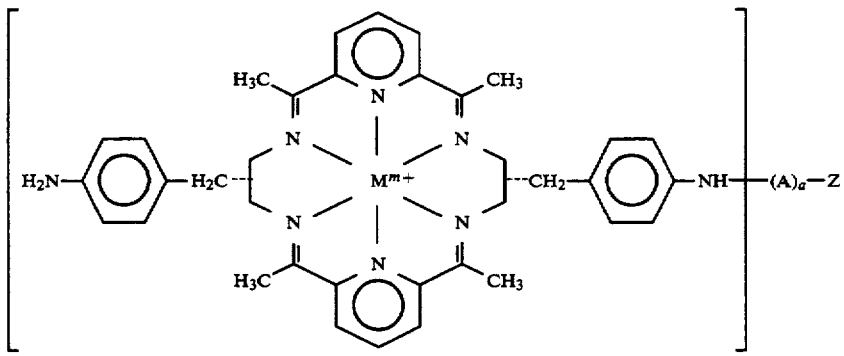

wherein

A is a linking group between the terminally reactive groups of the macrocyclic complex and a reactive biomolecule;

a is 0 or 1; and

Z is a reactive biomolecule which specifically binds analytes comprising cell antigens, polynucleotide sequences and binding proteins or a reactive biomolecule which functions as said analyte.

* * * * *